US012614281B2

(12) United States Patent　　　　(10) Patent No.:　US 12,614,281 B2
　Koster et al.　　　　　　　　　　　(45) Date of Patent:　　Apr. 28, 2026

(54) IMAGE ANALYSIS SYSTEM FOR IDENTIFYING LUNG FEATURES

(71) Applicant: Ceevra, Inc., San Francisco, CA (US)

(72) Inventors: Kenneth Alan Koster, San Francisco, CA (US); Russell Kenji Yoshinaka, Lafayette, CA (US); Hanna Katherine Winter, San Francisco, CA (US)

(73) Assignee: Ceevra, Inc., San Francisco, CA (US)

( * ) Notice: Subject to any disclaimer, the term of this patent is extended or adjusted under 35 U.S.C. 154(b) by 153 days.

(21) Appl. No.: 17/658,924

(22) Filed: Apr. 12, 2022

(65) Prior Publication Data

US 2022/0237805 A1　　Jul. 28, 2022

Related U.S. Application Data

(63) Continuation of application No. 16/949,685, filed on Nov. 10, 2020, now Pat. No. 11,348,250.

(Continued)

(51) Int. Cl.
　*G06T 7/11*　　　　　(2017.01)
　*A61B 5/00*　　　　　(2006.01)
　　　　　(Continued)

(52) U.S. Cl.
　CPC ............... *G06T 7/11* (2017.01); *A61B 5/004* (2013.01); *A61B 5/489* (2013.01); *A61B 6/032* (2013.01); *A61B 6/50* (2013.01); *G06T 7/13* (2017.01); *G06T 7/62* (2017.01); *G06T 7/70* (2017.01); *G06V 10/26* (2022.01); *G06V 10/44* (2022.01); *G06V 20/64* (2022.01); *G06T 2200/04* (2013.01); *G06T 2207/10081*

(2013.01); *G06T 2207/10088* (2013.01); *G06T 2207/20128* (2013.01); *G06T 2207/30061* (2013.01);

(Continued)

(58) Field of Classification Search
　CPC ..... G06T 7/11; G06T 7/13; G06T 7/62; G06T 7/70; G06T 2200/04; G06T 2207/10081; G06T 2207/10088; G06T 2207/20128; G06T 2207/30061; G06T 2207/30096; G06T 2207/30101; G06T 2207/10028; A61B 5/004; A61B 5/489; A61B 6/032; A61B 6/50; G06V 10/26; G06V 10/44; G06V 20/64; G06V 2201/031
　See application file for complete search history.

(56) References Cited

U.S. PATENT DOCUMENTS 8,150,113 B2　　4/2012　Ray et al.
8,244,733 B2　　8/2012　Fortier et al.
　　　　　　(Continued)

FOREIGN PATENT DOCUMENTS

WO　　WO-2017189758 A1　11/2017
WO　　WO-2017197360 A1　11/2017
WO　　WO-2019184158 A1　10/2019

OTHER PUBLICATIONS

Aurenhammer, Franz, "Voronoi diagrams—A survey of a fundamental geometric data structure," ACM Computing Surveys, vol. 23, No. 3, Sep. 1991, pp. 345-405.

(Continued)

*Primary Examiner* — Ross Varndell
(74) *Attorney, Agent, or Firm* — Weaver Austin Villeneuve & Sampson LLP

(57) ABSTRACT

Methods and apparatuses for identifying lung features are provided herein.

20 Claims, 8 Drawing Sheets

Related U.S. Application Data

(60) Provisional application No. 62/933,884, filed on Nov. 11, 2019.

(51) Int. Cl.

| | | |
|---|---|---|
| *A61B 6/03* | (2006.01) | |
| *A61B 6/50* | (2024.01) | |
| *G06T 7/13* | (2017.01) | |
| *G06T 7/62* | (2017.01) | |
| *G06T 7/70* | (2017.01) | |
| *G06V 10/26* | (2022.01) | |
| *G06V 10/44* | (2022.01) | |
| *G06V 20/64* | (2022.01) | |

(52) U.S. Cl.
CPC .............. *G06T 2207/30096* (2013.01); *G06T 2207/30101* (2013.01); *G06V 2201/031* (2022.01)

(56) References Cited

U.S. PATENT DOCUMENTS

| | | | | |
|---|---|---|---|---|
| 8,538,770 | B2 | 9/2013 | Papier et al. | |
| 9,129,054 | B2 | 9/2015 | Nawana et al. | |
| 9,538,925 | B2 | 1/2017 | Sharma et al. | |
| 9,797,380 | B2 | 10/2017 | Burkett | |
| 10,653,502 | B2 | 5/2020 | Kuo | |
| 11,348,250 | B2 | 5/2022 | Koster et al. | |
| 2004/0122704 | A1 | 6/2004 | Sabol et al. | |
| 2005/0049497 | A1 | 3/2005 | Krishnan et al. | |
| 2008/0201280 | A1 | 8/2008 | Martin et al. | |
| 2008/0235052 | A1 | 9/2008 | Node-Langlois et al. | |
| 2008/0317314 | A1 | 12/2008 | Schwartz et al. | |
| 2009/0185731 | A1 | 7/2009 | Ray et al. | |
| 2009/0226057 | A1 | 9/2009 | Mashiach et al. | |
| 2009/0252395 | A1 | 10/2009 | Chan et al. | |
| 2009/0299766 | A1 | 12/2009 | Friedlander et al. | |
| 2010/0070293 | A1 | 3/2010 | Brown et al. | |
| 2010/0191071 | A1 | 7/2010 | Anderson et al. | |
| 2011/0022622 | A1 | 1/2011 | Boroczky et al. | |
| 2011/0119212 | A1 | 5/2011 | De Bruin et al. | |
| 2011/0313790 | A1 | 12/2011 | Yao | |
| 2012/0232930 | A1 | 9/2012 | Schmidt et al. | |
| 2012/0274631 | A1 | 11/2012 | Friedland et al. | |
| 2012/0283574 | A1 | 11/2012 | Park et al. | |
| 2013/0325508 | A1 | 12/2013 | Johnson et al. | |
| 2014/0079306 | A1* | 3/2014 | Inoue ........................ | G06T 7/12 382/131 |
| 2014/0298270 | A1* | 10/2014 | Wiemker ................ | G06T 7/174 715/849 |
| 2015/0126894 | A1 | 5/2015 | Benson et al. | |
| 2016/0067007 | A1 | 3/2016 | Piron et al. | |
| 2016/0110632 | A1 | 4/2016 | Kiraly et al. | |
| 2016/0140300 | A1 | 5/2016 | Purdie et al. | |
| 2016/0328850 | A1 | 11/2016 | Yin et al. | |
| 2016/0338685 | A1 | 11/2016 | Nawana et al. | |
| 2017/0035514 | A1 | 2/2017 | Fox et al. | |
| 2017/0061375 | A1 | 3/2017 | Laster et al. | |
| 2017/0076046 | A1 | 3/2017 | Barnes et al. | |
| 2017/0193160 | A1 | 7/2017 | Long et al. | |
| 2017/0224301 | A1* | 8/2017 | Radhakrishnan ........ | A61B 6/50 |
| 2018/0040088 | A1 | 2/2018 | Kanada | |
| 2018/0047168 | A1* | 2/2018 | Chen ......................... | G06T 7/11 |
| 2018/0153632 | A1 | 6/2018 | Tokarchuk et al. | |
| 2018/0303552 | A1 | 10/2018 | Ryan et al. | |
| 2018/0344308 | A1 | 12/2018 | Nawana et al. | |
| 2018/0368930 | A1 | 12/2018 | Esterberg et al. | |
| 2019/0139227 | A1* | 5/2019 | Wang ...................... | G06F 18/24 |
| 2019/0325645 | A1* | 10/2019 | Guendel .............. | A61B 6/5223 |
| 2019/0370964 | A1 | 12/2019 | Yu et al. | |
| 2020/0349703 | A1* | 11/2020 | Hashimoto ............... | G06T 7/12 |
| 2020/0387729 | A1* | 12/2020 | Ichinose ................... | G06T 7/11 |
| 2020/0410670 | A1 | 12/2020 | Gerard et al. | |
| 2021/0142485 | A1 | 5/2021 | Koster et al. | |
| 2021/0169576 | A1 | 6/2021 | Koster et al. | |
| 2022/0092791 | A1* | 3/2022 | Dougherty ........... | G06T 7/0012 |

OTHER PUBLICATIONS

Benmansour, Fethalah, et al. "Tubular Structure Segmentation Based on Minimal Path Method and Anisotropic Enhancement," International Journal of Computer Vision 92.2, Mar. 31, 2010, pp. 192-210.

Benmansour, Fethallah, et al., "Tubular Geodesics Using Oriented Flux: An ITK Implementation," Article, Feb. 1, 2013, 8 pages.

Beucher, Serge. "The Watershed Transformation Applied to Image Segmentation," Scanning Microscopy—Supplement, 1992, pp. 1-26.

Cornea, Nicu D., et al. "Computing Hierarchical Curve-Skeletons of 3D Objects," The Visual Computer 21.11, Oct. 2005, 19 pages.

European Office Action dated Apr. 12, 2022 in Application No. EP19846994.2.

Extended European Search Report dated Mar. 23, 2022, in Application No. 19846994.2.

FujiFilm, Synapse 3D, Product Data Sheet, Version 4, Enterprise Solution, http://www.fujifilmusa.com/products/medical/radiology/3D, MKT-0033341-B, 15 pages.

FujiFilm, Synapse 3D V4.1US, Synapse 3D (US) Product Specifications: Z30N1138B, Fujifilm Corporation, Sep. 2014, 62 pages.

Giuliani, Nicola, et al. "Pulmonary Lobe Segmentation in CT Images using Alpha-Expansion," Visigrapp 2018, vol. 4, pp. 387-394.

Gu, Suicheng, et al. "Automated Lobe-Based Airway Labeling," International Journal of Biomedical Imaging, 2012 (2012): 10 pages.

Helen, R., et al. "Segmentation of Pulmonary Parenchyma in CT Lung Images Based on 2D Otsu Optimized by PSO," 2011 International Journal of Advanced Science and Technology, vol. 29 No. 10S, 2020, pp. 4334-4347.

Helmberger, Michael, et al. "Quantification of Tortuosity and Fractal Dimension of The Lung Vessels In Pulmonary Hypertension Patients," PLOS | One, Jan. 14, 2014, vol. 9, Issue 1, 87515, pp. 1-9.

International Preliminary Report on Patentability dated May 27, 2022, in PCT Application No. PCT/US2020/059988.

International Preliminary Report on Patentability mailed Feb. 18, 2021, issued in PCT Application No. PCT/US2019/045129.

International Search Report and Written Opinion dated Oct. 25, 2019, issued in PCTUS2019045129.

International Search Report and Written Opinion mailed Feb. 3, 2021 issued in PCTUS2020059988.

Lassen, Bianca, et al. "Automatic Segmentation of Lung Lobes From Chest CT Images Based on Fissures, Vessels, and Bronchi," IEEE, Institute for Medical Image Computing, 32.2 (2012), pp. 560-563.

Law, Max WK, et al., "Three Dimensional Curvilinear Structure Detection Using Optimally Oriented Flux," Department of Computer Science and Engineering, LNCS 5305, 2008, pp. 368-382.

Mansoor, Awais, et al., "Segmentation and Image Analysis of Abnormal Lungs at CT: Current Approaches, Challenges, and Future Trends," RadioGraphics, vol. 35, No. 4, Jul.-Aug. 2015, pp. 1056-1076.

Meng, Qier, et al. "Airway Segmentation From 3D Chest CT Volumes Based on Volume of Interest Using Gradient Vector Flow," Medical Imaging Technology, 36.3 (2018), 4 pages.

OBGYN Key, "Augmented Reality in Minimally Invasive Digestive Surgery," https://obgynkey.com/augmented-reality-in-minimally-invasive-digestive-surgery/, Nov. 10, 2020, pp. 1-6.

Ochs, Robert A., et al. "Automated classification of lung bronchovascular anatomy in CT using AdaBoost," Medical Image Analysis, 11.3, Jun. 2007, pp. 315-324.

Payer, Christian, et al. "Automated Integer Programming Based Separation of Arteries and Veins From Thoracic CT Images," Medical Image Analysis, May 4, 2016, pp. 1-19.

Payer, Christian, et al. "Automatic Artery-Vein Separation From Thoracic CT Images Using Integer Programming," Conference Paper, DOI: 10.1007/978-3-319-24571-3_5, Oct. 2015, 9 pages.

(56)  References Cited

OTHER PUBLICATIONS

Pu, Jiantao, et al., "A Differential Geometric Approach to Automated Segmentation of Human Airway Tree," IEEE Transactions on Medical Imaging, 30(2), Feb. 2011, pp. 1-36.

Rohlfing, Torsten, et al. "Evaluation of Atlas Selection Strategies For Atlas-Based Image Segmentation With Application to Confocal Microscopy Images of Bee Brains," Neuroimage, Nov. 7, 2003, 32 Pages.

Shekhovtsov, Alexander, et al., "Maximum Persistency Via Iterative Relaxed Inference With Graphical Models," Proceedings of The IEEE, 2017, pp. 14.

Shirk, Joseph D., et al. "Effect of 3-Dimensional Virtual Reality Models For Surgical Planning of Robotic-Assisted Partial Nephrectomy on Surgical Outcomes: A Randomized Clinical Trial," JAMA Network Open, Sep. 18, 2019 pp. 1-11.

Soler, Luc, et al., "Patient Specific Anatomy: The New Area of Anatomy Based on Computer Science Illustrated on Liver," Journal of Visualized Surgery, J Vis Surg 2015;1:21, 12 Pages.

Türetken, Engin, et al. "Reconstructing Curvilinear Networks Using Path Classifiers and 10 Integer Programming," IEEE Transactions on Pattern Analysis and Machine Intelligence, 2016, pp. 1-22.

Turetken, Engin, et al. "Reconstructing Loopy Curvilinear Structures Using Integer Programming," Proceedings of The IEEE Conference, 2013, pp. 1822-1825.

US Notice of Allowance dated Feb. 10, 2022 issued in U.S. Appl. No. 16/949,685.

US Notice of Allowance dated May 4, 2022 issued in U.S. Appl. No. 16/949,685.

Van Dongen, Evelien, et al., "Automatic Segmentation of Pulmonary Vasculature in Thoracic CT Scans With Local Thresholding and Airway Wall Removal," 2010 IEEE International Symposium on Biomedical Imaging: From Nano to Macro. IEEE, 2010. 15, pp. 668-671.

Van Ginneken, Bram, et al., "Robust Segmentation and Anatomical Labeling of The Airway Tree From Thoracic CT Scans," International Conference on Medical Image Computing and Computer-Assisted Intervention, Springer, Berlin, 10 Heidelberg, 2008, 9 pages.

EP Extended European Search report dated Mar. 19, 2024 in EP Application No. 20888543.4.

IN Office Action dated Dec. 18, 2024 in IN Application No. 202217028374.

U.S. Non-Final Office Action dated Jan. 29, 2024 in U.S. Appl. No. 17/250,572.

Van Rikxoort, E., et al., "Automatic Segmentation of Pulmonary Segments From Volumetric Chest CT Scans," IEEE Transactions on Medical Imaging, 2009, vol. 28 (4), pp. 621-630.

* cited by examiner

500

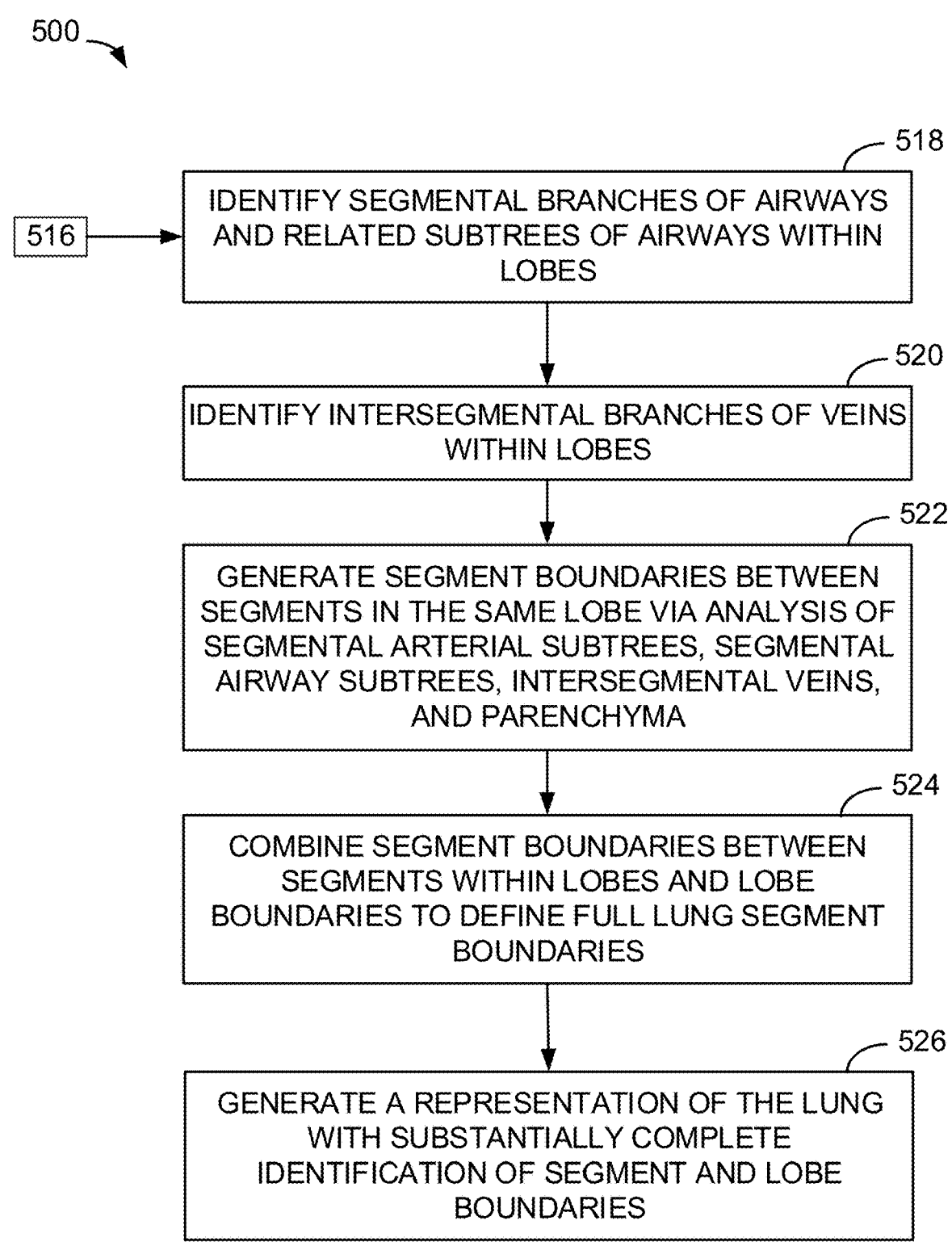

518

IDENTIFY SEGMENTAL BRANCHES OF AIRWAYS AND RELATED SUBTREES OF AIRWAYS WITHIN LOBES

516

520

IDENTIFY INTERSEGMENTAL BRANCHES OF VEINS WITHIN LOBES

522

GENERATE SEGMENT BOUNDARIES BETWEEN SEGMENTS IN THE SAME LOBE VIA ANALYSIS OF SEGMENTAL ARTERIAL SUBTREES, SEGMENTAL AIRWAY SUBTREES, INTERSEGMENTAL VEINS, AND PARENCHYMA

524

COMBINE SEGMENT BOUNDARIES BETWEEN SEGMENTS WITHIN LOBES AND LOBE BOUNDARIES TO DEFINE FULL LUNG SEGMENT BOUNDARIES

526

GENERATE A REPRESENTATION OF THE LUNG WITH SUBSTANTIALLY COMPLETE IDENTIFICATION OF SEGMENT AND LOBE BOUNDARIES

*FIGURE 5B*

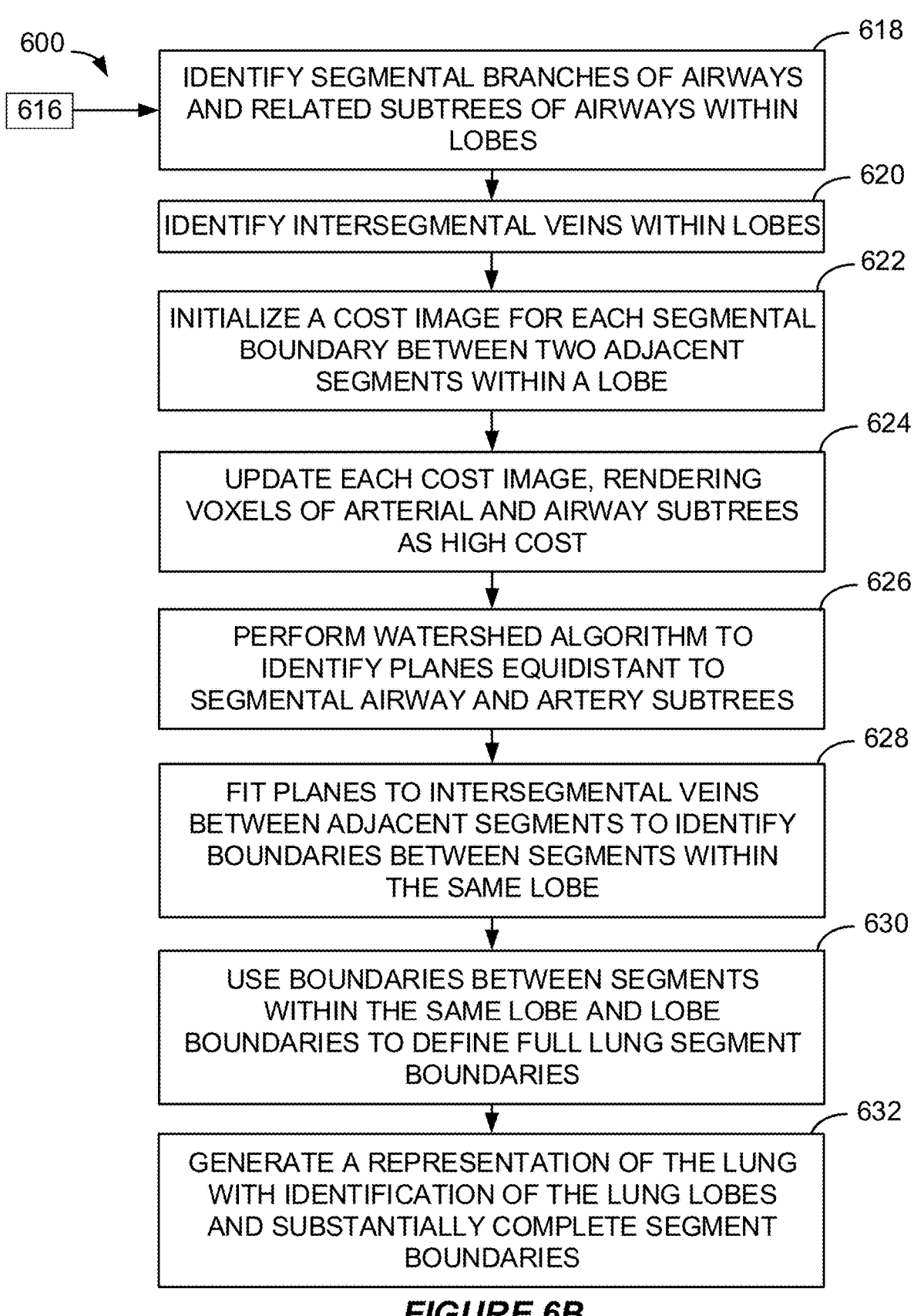

600

616 →

618
IDENTIFY SEGMENTAL BRANCHES OF AIRWAYS AND RELATED SUBTREES OF AIRWAYS WITHIN LOBES

620
IDENTIFY INTERSEGMENTAL VEINS WITHIN LOBES

622
INITIALIZE A COST IMAGE FOR EACH SEGMENTAL BOUNDARY BETWEEN TWO ADJACENT SEGMENTS WITHIN A LOBE

624
UPDATE EACH COST IMAGE, RENDERING VOXELS OF ARTERIAL AND AIRWAY SUBTREES AS HIGH COST

626
PERFORM WATERSHED ALGORITHM TO IDENTIFY PLANES EQUIDISTANT TO SEGMENTAL AIRWAY AND ARTERY SUBTREES

628
FIT PLANES TO INTERSEGMENTAL VEINS BETWEEN ADJACENT SEGMENTS TO IDENTIFY BOUNDARIES BETWEEN SEGMENTS WITHIN THE SAME LOBE

630
USE BOUNDARIES BETWEEN SEGMENTS WITHIN THE SAME LOBE AND LOBE BOUNDARIES TO DEFINE FULL LUNG SEGMENT BOUNDARIES

632
GENERATE A REPRESENTATION OF THE LUNG WITH IDENTIFICATION OF THE LUNG LOBES AND SUBSTANTIALLY COMPLETE SEGMENT BOUNDARIES

*FIGURE 6B*

IMAGE ANALYSIS SYSTEM FOR IDENTIFYING LUNG FEATURES

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

FIELD

The embodiments of the present disclosure relate to the field of digital imaging, and more particularly to processing a 3D digital medical image of a lung to identify the boundaries of a plurality of lung segments.

BACKGROUND

Review and interpretation of 3D digital medical images, such as the images produced by computed tomography (CT) scanners and magnetic resonance imaging (MRI) machines, is a common task of surgeons and other physicians. Informed by their interpretation of a patient's medical image, a physician will make diagnoses and treatment decisions about that patient. For a patient with a suspected cancerous lesion in their lung, some of the questions considered by a physician will include whether the lesion should be surgically removed, whether the lesion should be ablated (which is to say, frozen or heated in order to destroy the cancerous tissue), or whether the patient should be treated by radiation therapy and/or chemotherapy.

For patients considered for surgery, a surgeon will evaluate the patient's anatomy within the medical image to help decide what parts of the lung should be removed along with the cancer. The goals of the surgeon are twofold: (1) to remove the suspected area of cancer in its entirety, while (2) retaining as much healthy lung tissue as possible. In order to help ensure that cancer cells are not left behind, the surgeon will remove an extra area of healthy tissue around the suspected malignancy, commonly referred to as a "margin." The size of the margin considered oncologically appropriate varies according to characteristics of the tumor, tissue, and organ type.

In deciding what type of operation to perform and how best to perform it, the surgeon will rely largely on the medical imaging of the patient (e.g., CT scan or MRI). Increasingly, surgeons are also utilizing three-dimensional (3D) reconstructions of such medical images. The use of 3D reconstructions during surgical planning has been shown to provide surgeons with a better understanding of the patient's anatomy and to result in improved surgical outcomes. Examples of such benefits are described by Shirk 2019. Presently, 3D reconstructions of lungs typically include a depiction of the lung surface, the lung lobes, and other anatomical structures such as lesions, airways and blood vessels. Existing 3D reconstruction techniques do not, however, include an automatically generated depiction of the segments within the lobes.

SUMMARY

Briefly, in certain embodiments, a method for identifying segments in a lung including a number of lobes, each lobe including a number of the segments, each segment having a boundary, may include receiving image data forming a three-dimensional representation of at least a part of the lung, computationally identifying, using the image data, (i) lung parenchyma and/or an outer surface of the lung and (ii) at least one anatomical structure within the lung, where the at least one anatomical structure is one or more fissures between the lobes, one or more veins, one or more arteries, and/or one or more airways, computationally identifying, from (i) the lung parenchyma and/or the outer surface of the lung and (ii) the at least one identified anatomical structure, substantially all the boundary of at least one segment within the lung, where computationally identifying substantially all of the boundary of the at least one segment within the lung includes computationally identifying, from the at least one identified anatomical structure, substantially all of a segment-to-segment surface boundary between the at least one segment and an additional segment within the lung, the additional segment being adjacent to the at least one segment and the segment-to-segment surface boundary lying on the outer surface of the lung, and generating a representation containing substantially all the boundary of the at least one segment within the lung.

In some embodiments, the image data includes a CT scan and/or an Mill. In some embodiments, the CT scan and/or MM include a CT scan with contrast and/or an MM with contrast. In some embodiments, the method also includes providing a visual presentation containing substantially all the boundary of the at least one segment within the lung. In some embodiments, the at least one anatomical structure includes the one or more veins. In some embodiments, the at least one anatomical structure includes the one or more arteries. In some embodiments, the at least one anatomical structure includes the one or more airways. In some embodiments, computationally identifying (i) lung parenchyma and/or an outer surface of the lung includes computationally identifying one or more fissures between lobes and the at least one anatomical structure includes the one or more veins. In some embodiments, computationally identifying (i) lung parenchyma and/or an outer surface of the lung including computationally identifying one or more fissures between lobes and the at least one anatomical structure includes the one or more arteries. In some embodiments, computationally identifying (i) lung parenchyma and/or an outer surface of the lung includes computationally identifying one or more fissures between lobes and the at least one anatomical structure includes the one or more airways. In some embodiments, the at least one anatomical structure includes the one or more veins and the one or more arteries. In some embodiments, the at least one anatomical structure includes the one or more veins and one or more airways. In some embodiments, the at least one anatomical structure includes the one or more arteries and the one or more airways. In some includes, the at least one segment includes a given segment, generating the representation includes determining a location of a first anatomical structure within the given segment, and the first anatomical structure is at least a portion of the one or more veins, at least a portion of the one or more arteries, and/or at least a portion of the one or more airways. In some embodiments, the at least one segment includes a given segment, generating the representation includes determining a location of a first anatomical structure within the given segment, and the first anatomical structure is at least a portion of one or more intersegmental veins. In some embodiments, the at least one segment includes a given segment and generating the representation includes determining a location of at least one or more lesions within the given segment. In some embodiments, the at least one segment includes a given segment and generating the representation includes determining a location of at least one or more lymph nodes within the given segment. In some embodiments, the at least one segment includes a given segment and the method may further include computationally determining, using the image data, a placement of a first anatomical structure within the boundary of the given segment, where the first anatomical structure is at least a portion of the one or more veins, at least a portion of the one or more arteries, at least a portion of the one or more airways, one or more lesions, and/or one or more lymph nodes. In some embodiments, the method further includes computationally identifying, using the image data, one or more intersegmental veins within the lung, where computationally identifying substantially all the boundary of at least one segment within the lung includes computationally identifying substantially all the boundary of at least one segment based at least in part on the identified one or more intersegmental veins. In some embodiments, the lung has an outer surface and the method further includes computationally identifying, using the image data, at least portions of the outer surface of the lung, where computationally identifying substantially all the boundary of at least one segment within the lung includes computationally identifying substantially all the boundary of at least one segment based at least in part on the identified portions of the outer surface of the lung. In some embodiments, the lung further includes parenchyma and the method further includes computationally identifying, using the image data, at least portions of the parenchyma, where computationally identifying substantially all the boundary of at least one segment within the lung includes computationally identifying substantially all the boundary of at least one segment based at least in part on the identified portions of the parenchyma. In some embodiments, the at least one segment includes a given segment and the method also includes, calculating, based on the computationally identified boundary of the given segment, a volume of the given segment. In some embodiments, the at least one segment includes a given segment and the method further includes calculating a distance between any boundary of the given segment and another anatomical structure within the lung. In some embodiments, the method further includes calculating a distance-based measure of the at least one segment, where the distance-based measure is a maximum diameter, a centroid, a bounding box, a surface area of the boundaries of the at least one segment, a length of the at least one segment on a given surface of the lung, a maximum length of the at least one segment on the surface of the lung, and/or a surface area or length of where the at least one segment meets a second segment. In some embodiments, the at least one segment includes a given segment, the lung has an outer surface, and the method further includes calculating a minimum distance between the given segment and the outer surface of the lung. In some embodiments, the image data includes image data obtained with at least one of a CT scan, an MRI, an ultrasound scan, and a nuclear medicine scan.

In certain embodiments, a method for identifying features in a lung including a number of lobes, each lobe including a number of segments, each segment having a boundary, may include receiving image data forming a volumetric representation of at least a part of a human lung, computationally identifying, using the image data, an anatomical feature within the lung, where the anatomical feature is one or more fissures between the lobes, a network of veins, a network of arteries, a network of airways, and/or one or more intersegmental veins, computationally identifying, using the anatomical feature, a boundary of at least one segment within the lung, and generating a representation containing (i) substantially all the boundary of the at least one segment within the lung, and (ii) the one or more fissures between the lobes, the network of veins, the network of arteries, the network of bronchi, the one or more intersegmental veins, or any combination of the foregoing.

In certain embodiments, a method for identifying features in a human lung including a number of lobes, each lobe including a number of segments, may include receiving image data forming a volumetric representation of at least a part of the human lung, computationally identifying, using the image data, portions of at least two lobes and a fissure between said two lobes; computationally identifying, using the image data, a network of arteries, a network of veins, and/or a network of bronchi, where identifying the network of arteries, veins, and/or bronchi includes computationally identifying a tube-like structure in image data, where the tube-like structure is identified by identifying a set of gradient changes within the image data, and computationally determining, based on how the tube-like structure branches within the human lung, that the tube-like structure is part of the network of arteries, veins, and/or bronchi, and computationally identifying, based on the identified network of arteries, veins, and/or bronchi and the identified lobes or the fissure between said lobes, boundaries of a plurality of segments within at least one of said lobes.

In some embodiments computationally identifying the boundary of a single segment in the plurality of segments includes computationally identifying a volume within image data that exclusively receives blood from a single branch of the network of arteries. In some embodiments, computationally identifying the boundary of a single segment in the plurality of segments includes computationally identifying a volume within the image data that does not pass through the fissure between said lobes. In some embodiments, the method also includes computationally identifying, using the image data, a lesion within the human lung, computationally determining, from the image data, that the lesion is located in a given segment of the plurality of segments, and computationally measuring, from the image data, a minimum distance between the lesion and the boundary of the given segment.

In certain embodiments, a method for identifying features in a human lung including a number of lobes, each lobe including a number of segments, may include receiving image data forming a volumetric representation of at least a part of a human lung, computationally identifying, using the image data, a network of arteries, where identifying the network of arteries includes computationally identifying a tube-like structure in the image data, where the tube-like structure is identified by identifying a set of gradient changes within the image data, and computationally determining, using the image data and based on how the tube-like structure branches within the human lung, that the tube-like structure is part of the network of arteries, computationally identifying, using the image data, a network of bronchi, where identifying the network of bronchi includes computationally identifying an additional tube-like structure in the image data, where the additional tube-like structure is identified by identifying an additional set of gradient changes within the image data, and computationally determining, using the image data and based on how the additional tube-like structure branches within the human lung, that the additional tube-like structure is part of the network of bronchi, and computationally identifying, based on the identified network of arteries and the identified network of bronchi, boundaries of a plurality of segments within at least one of said lobes.

BRIEF DESCRIPTION OF THE DRAWINGS

FIGS. 5A and 5B are a process flow diagram depicting operations of methods performed in accordance with certain disclosed embodiments.

FIGS. 6A and 6B are a process flow diagram depicting operations of methods performed in accordance with certain disclosed embodiments.

DETAILED DESCRIPTION

In the following description, numerous specific details are set forth to provide a thorough understanding of the presented embodiments. The disclosed embodiments may be practiced without some or all of these specific details. In other instances, well-known process operations have not been described in detail to not unnecessarily obscure the disclosed embodiments. While the disclosed embodiments will be described in conjunction with the specific embodiments, it will be understood that it is not intended to limit the disclosed embodiments.

I. Lung Anatomy

The lung anatomy of a patient discernible within medical images includes the lung's airways, pulmonary veins (blood vessels that carry oxygenated blood), and pulmonary arteries (blood vessels which carry deoxygenated blood), each of which form a tree-like system or network within each lung. The veins and arteries can be more generally referred to as vessels or vasculature.

Each lung is composed of multiple lobes. Each lobe has its own independent and distinct subtree of each of the three branching systems (airways, vein, and artery). Pulmonary arteries, veins, and airways do not cross lobe boundaries. A branch upstream of all veins in a lobe is sometimes referred to as a lobar branch of the pulmonary arteries. A branch upstream all airways in a lobe is sometimes referred to as a lobar branch of the lobar airway. The lobes are separated by fissures which are discernable on some medical images. Lung tissue which is not a blood vessel or an airway is called parenchyma.

In human anatomy, the left lung is smaller than the right, and is separated into two lobes: an upper lobe and a lower lobe. The right lung consists of three lobes: upper, lower, and middle.

Figure 1:
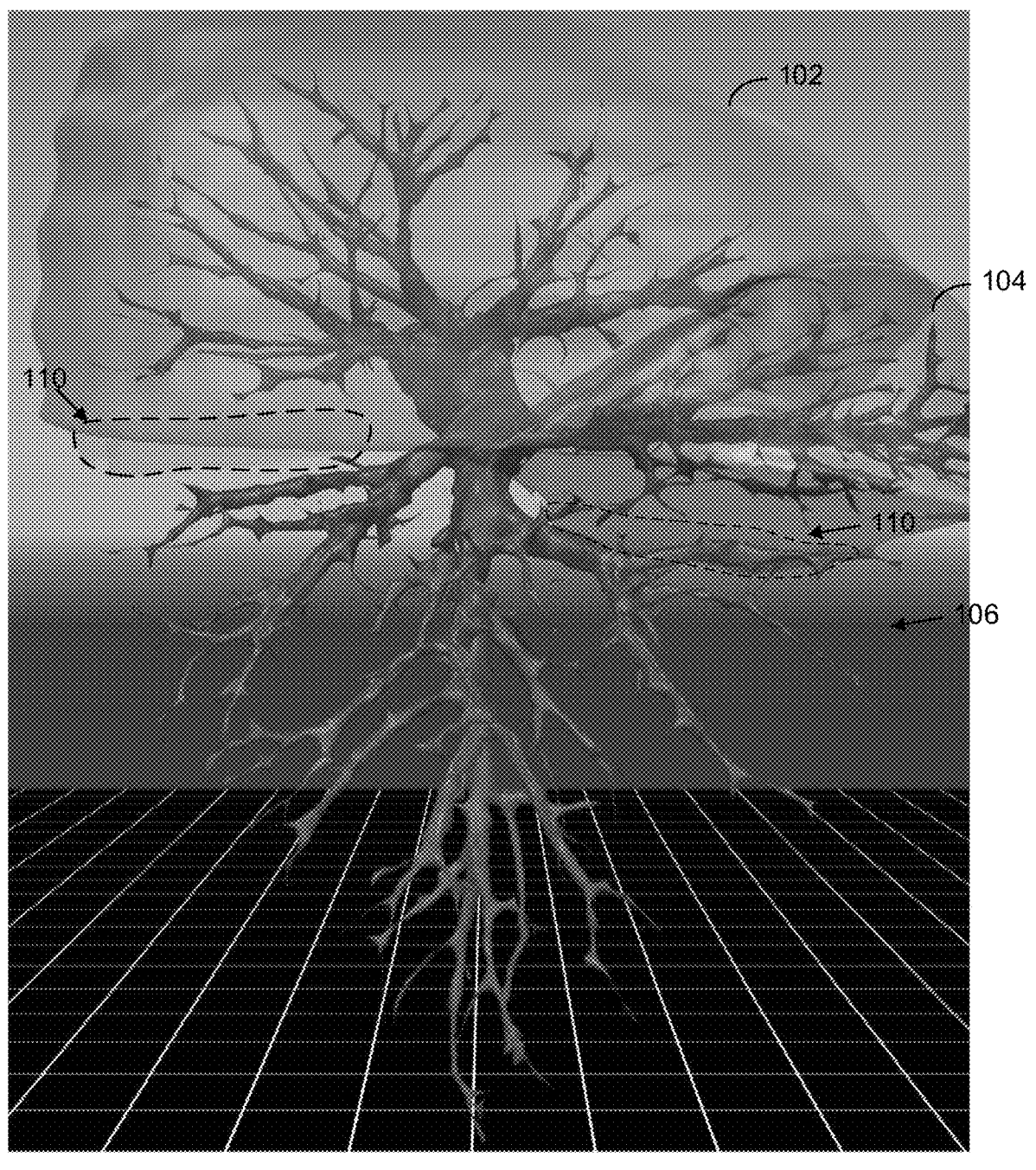
FIGS. 1-4 are images of a human lung.

An image of a right lung is shown in FIG. 1. As shown in FIG. 1, there is a relatively large amount of space (illustrated as regions 110) between the arterial subtrees of the upper lobe 102 and the middle lobe 104 and the arterial subtree of the lower lobe 106 (lobe parenchyma is not shown in FIG. 1).

Each lobe can further be subdivided into segments. Similar to lobes, each segment also has an independent supply of blood and an independent branch of the bronchus. Analogous to lobes, one segment within a lobe can be removed, leaving the other segments as functional units of the lung. Unlike lobes, however, segments are typically not separated by fissures. In rare cases, "accessory" fissures are visible in medical images and demarcate the border between two segments within a lobe. Aspects of this disclosure assume the common case, that no accessory fissures are present within the medical image being processed.

In the left lung, each lobe contains four segments, for a total of eight segments in the lung. In the right lung, there are a total of ten segments, with five in the lower lobe (four of which are referred to as the "basal" segments"), two in the middle lobe, and three in the upper lobe.

Figure 2:
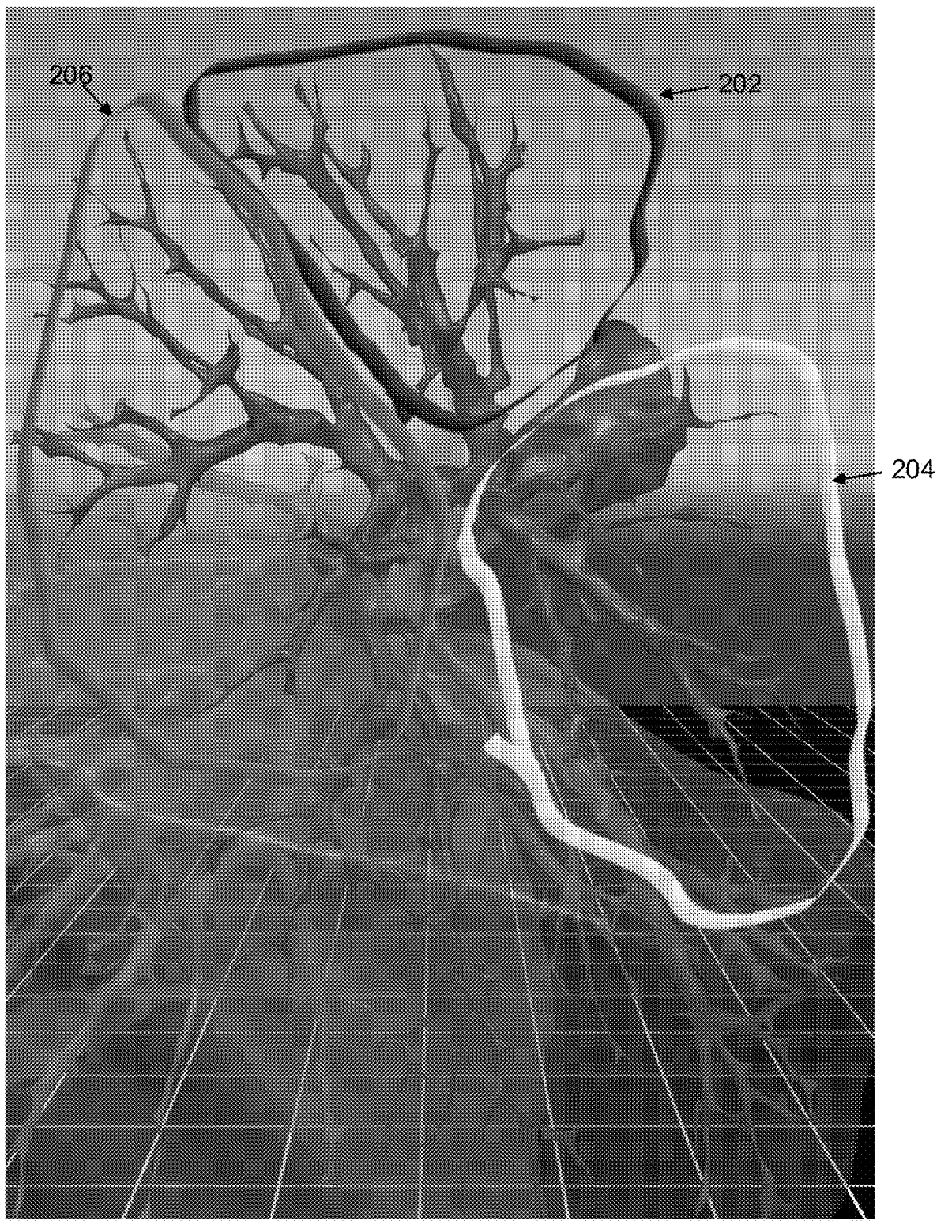

An image of the upper lobe of a right lung is shown in FIG. 2. FIG. 2 illustrates the spaces between the three segments of the upper lobe of the right lung. In FIG. 2, outline 202 shows the spaces around the arterial subtree of the apical segment, outline 204 shows the spaces around the arterial subtree of the anterior segment, and outline 206 shows the spaces around the arterial subtree of the posterior segment.

Figure 3:
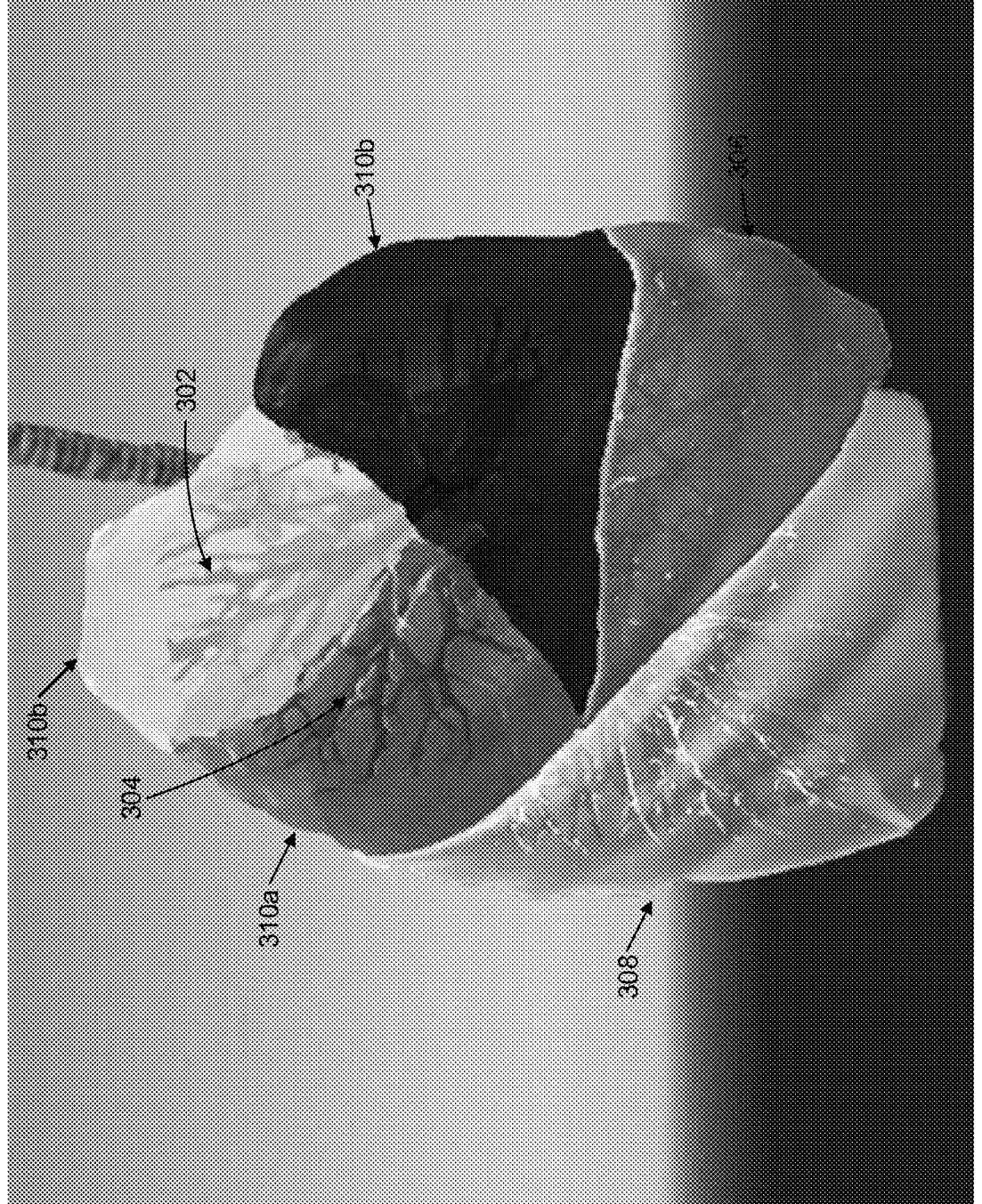

An image of a right lung is shown in FIG. 3. FIG. 3 illustrates the vein network 302, the arterial network 304, the middle right lobe 306, the lower right lobe 308, and the three segments 310*a*, 310*b*, and 310*b* of the upper right lobe.

Figure 4:
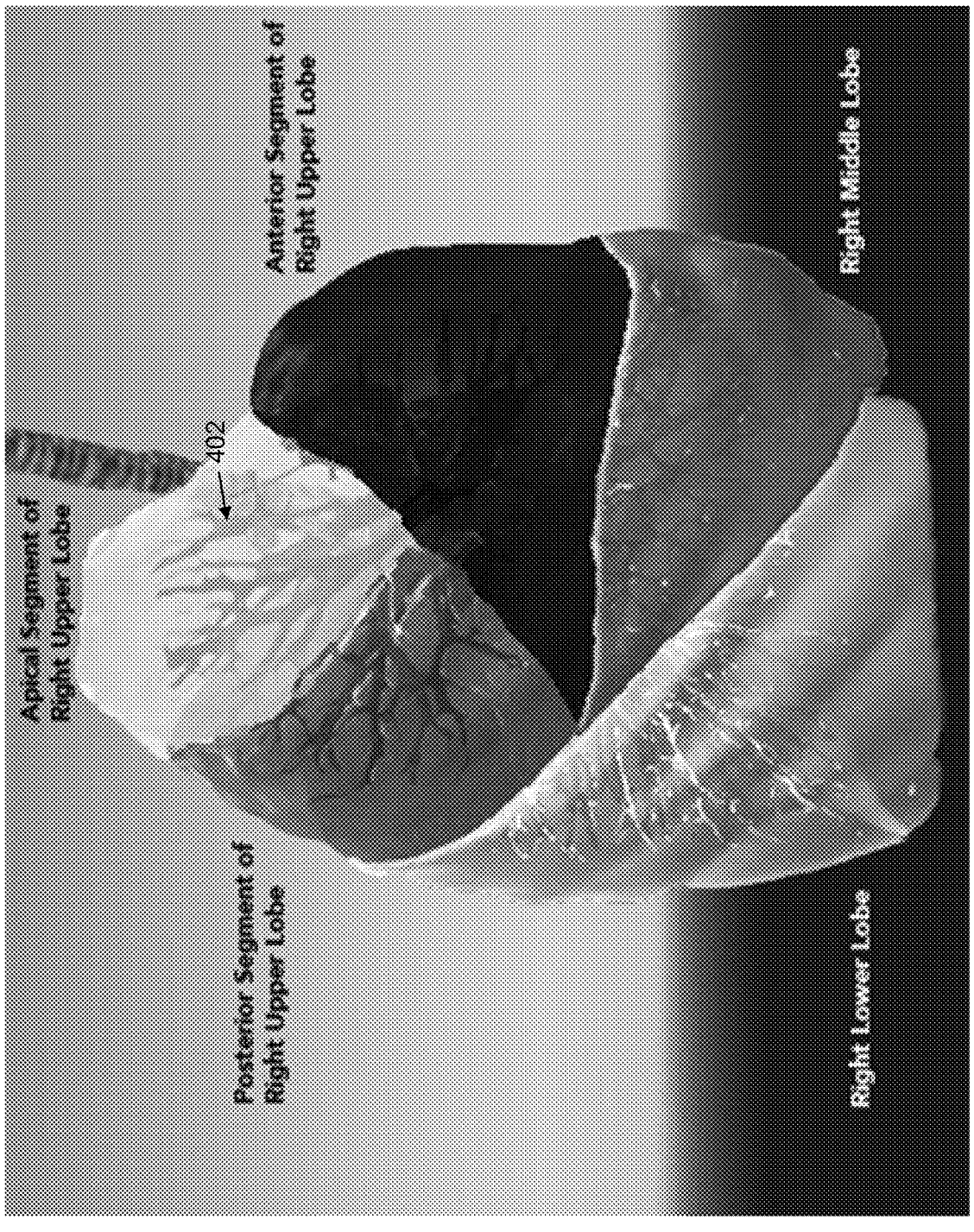

An image of a right lung is shown in FIG. 4. FIG. 4 illustrates the arterial network 304, the right lower lobe, the right middle lobe, the three segments (posterior, apical, and anterior) of the right upper lobe. While the networks of airways and veins are not explicitly illustrated in FIG. 4, their absence is visible in FIG. 4 (e.g., there are impressions of the veins and airways visible in FIG. 4).

Segments are far more difficult to discern on medical imaging than lobes. Unlike lobes, segments are not separated by visible fissures. Without this visual cue, physicians must identify segments based on their understanding of vessels and airways that define segments. Specifically, one definition of the area of a segment is that it is the area of a lobe which corresponds to a branch of the lobar pulmonary artery (segmental artery) and a branch of the lobar airway. Each part of the lung parenchyma belongs to one segment, which means it is also fed by one branch of the airway and one branch of the pulmonary artery. Just as the subtrees of arteries and airways are distinct and independent between different lobes, within lobes the segmental subtrees of arteries and airways are distinct and independent from the subtrees of arteries and airways of other segments. Some veins may reside entirely within a segment, while other veins, sometimes referred to as intersegmental veins pass along a portion of a boundary between lung segments. There are considerable variations in anatomy between human beings in the structure and branching of segment-level vessels, which complicates segment identification, as identification must consider the possible variations in vascular anatomy in human beings. Because of the foregoing, the identification and understanding of lung segments requires a high level of training and expertise, and even the most sophisticated physicians are commonly challenged with this exercise.

II. Lung Cancer Operations

The operation performed by the surgeon will have a different name according to the nature and quantity of the lung which is removed.

A pneumonectomy is the removal of an entire lung.

A lobectomy is the removal of a lung lobe. A lobectomy leaves a patient with more lung tissue than a pneumonectomy, as the lung will remain functional so long as at least one lobe remains. This is considered the standard of care for surgery for most lung lesions larger than 2 cm in diameter.

A segmentectomy is the removal of one or more segments. A segmentectomy is sometimes referred to as an "anatomical resection" in that the resection lines follow segment boundaries of the patient anatomy. Segmentectomy is an approach often favored by experienced surgeons for smaller lung lesions, typically 2 cm in diameter or smaller, when possible. The belief by many surgeons is that, for smaller lesions, a segmentectomy strikes the optimal balance between ensuring that all cancer is removed while preserving as much lung function as possible. A segmentectomy requires the surgeon to confidently understand which segment is involved, and that an adequate margin will be obtained by removing it. In some instances, multiple segments may be involved because either the mass or the margin crosses over them. In these cases, the surgeon may remove both segments, and this would still be considered a segmentectomy. Also, some types of segmentectomies are more difficult than others, often driven by how difficult it is for the surgeon to physically access the particular segment.

A wedge resection is the removal of a triangle-shaped portion of the lung that is not defined by a lobe or segment. As opposed to a segmentectomy, a wedge resection is a "non-anatomical" resection, as the resection lines do not follow anatomical boundaries. Wedge is not the favored approach, for oncological and/or functional reasons. Wedge is typically done in circumstances when a segmentectomy is not possible for some reason.

III. Use of Medical Imaging in Surgical Planning

When deciding on surgical approach (e.g., lobectomy vs. segmentectomy vs. wedge), the surgeon will rely largely on the patient's medical image, e.g., a CT scan, an MM, and/or a PET scan. The surgeon will consider, among other things, the lesion and location. In considering location, the surgeon will identify the relevant lobe(s) and potentially also the relevant segment(s). Identifying the relevant lobe is a prerequisite to a lobectomy and, as previously noted, is relatively easy due to the presence of visible fissures. Identifying the relevant segment is a prerequisite to a segmentectomy and, as also previously noted, is relatively difficult due to the absence of visible fissures separating the segments.

In addition to looking at the patient's CT scans or other medical images, the surgeon may also look at a 3D reconstruction of such images. Presently, 3D reconstructions of lungs will typically include an automatically-generated visual depiction of lobes, as defined by fissures, but lack an automatically-generated visual depiction of segments.

Although inclusion of lung segments within 3D reconstructions would be extremely helpful for surgeons, this is very difficult to achieve due to the wide variability in human segmental anatomy and the way segments are currently identified by physicians, as more fully detailed below.

The present disclosure enables a computer system configured to identify and label lung segments from a three-dimensional medical image such as a CT scan, and to visually depict such lung segments within a 3D reconstruction. This visual depiction of lung segments will help surgeons decide whether a segmentectomy is a possible intervention for the patient, and if so, which segment(s) should be removed, and the best approach to removing them. Certain details furthering that understanding may include: (1) the knowledge of which segment(s) contain a lesion; (2) the distances between the lesion and the borders of the segment(s) considered for removal, to help evaluate prospective surgical margins; (3) the spatial relationship of the segments to each other, to aid in planning and understanding the technical aspects of the surgery and to evaluate different possible surgical techniques.

IV. Use of Machine Learning in Medical Imaging

Various machine learning techniques are being employed towards medical imaging. To date, such techniques have largely been applied towards diagnosis, in particular the detection and identification of a particular disease state, such as a cancerous lesion. However, machine learning techniques, such as supervised learning, may also be applied towards the process of image segmentation.

Supervised learning is useful where an output (such as a segmentation of an image or a label of a segmentation) is available for a training dataset (e.g., a plurality of medical images). For example, a machine learning model may be trained with various collections of three-dimensional image data taken from CT scans and/or MRIs, and in these images, particular collections of voxels may be prelabeled as parenchyma, arteries, veins, fissures, airways, lesions, or lymph nodes. Using this training data, a machine learning model is trained to receive unlabeled and optionally unsegmented image data as an input and provide a segmented, labeled data set as an output. The output may identify collections of voxels that are labeled as parenchyma, arteries, veins, lung surface, fissures, airways, lesions, lymph nodes, or any combination thereof. In another approach, a machine learning model is trained with various collections of three-dimensional image data containing labelled collections of voxels (e.g., parenchyma, arteries, veins, lung surface, fissures, airways, lesions, and/or lymph nodes) and segment boundaries for lung images. Using this training data, a machine learning model is trained to receive labeled image data as inputs and produce fully or substantially fully defined segment boundaries for the lungs.

Examples of machine learning algorithms that are supervised include but are not limited to linear regression, logistic regression, decision trees, support vector machine (SVM), naive Bayes, k-nearest neighbors, and neural networks (multilayer perceptron). Reinforcement learning falls between supervised and unsupervised learning, where some feedback is available for each predictive step or action but there is no precise label. Rather than being presented with correct input/output pairs as in supervised learning, a given input is mapped to a reward function that an agent is trying to maximize. An example of a machine learning algorithm that is reinforcement-based includes a Markov Decision Process. Other types of learning that may fall into the one or more of the categories described above include, for example, deep learning and artificial neural networks (e.g., convolutional neural networks).

Various training tools or frameworks may exist to train the machine learning model. Examples of proprietary training tools include but are not limited to Amazon Machine Learning, Microsoft Azure Machine Learning Studio, DistBelief, Microsoft Cognitive Toolkit. Examples of open source training tools include but are not limited to Apache Singa, Caffe, H2O, PyTorch, MLPACK, Google TensorFlow, Torch, and Accord.Net.

The trained machine learning model may take one of several forms. In some implementations, the trained machine learning model is a classification and regression tree or a random forest tree. In some implementations, the trained machine learning model is an artificial neural network, such as a convolutional neural network. In some implementations, the trained machine learning model is a linear classifier, such as a linear regression, logistic regression, or support vector machine.

V. Image Analysis System

This disclosure relates to systems and methods that generate, from one or more three-dimensional (3D) digital images of a lung, a representation of the boundaries of the segments within that lung. Once defined, the boundaries can also be represented visually or used to calculate volume measurements (e.g. the volume of a segment), distance measurements (e.g. the maximum diameter of the segment, distances between a lesion or other structure and one or more segment boundaries), or other analyses based on the three-dimensional representation of the segment's boundaries.

The types of medical images that may be used to generate the 3D digital image include any relevant medical image, including, but not limited to, a computed tomography scan (commonly referred to as a CT scan), a magnetic resonance imaging scan (commonly referred to as an MRI), a nuclear medicine image including, but not limited to, a positron emission tomography scan (commonly referred to as a PET scan), and/or an ultrasound image, and a three-dimensional reconstruction of any of the foregoing.

VI. Terminology

As used herein, the term "surgery" refers to a procedure for treating injuries, disorders, and other medical conditions by incision and associated manipulation, particularly with surgical instruments. The terms "operation," "surgical operation," and "surgery" are used throughout this disclosure. Unless otherwise clear from context, the terms are used interchangeably.

As used herein, an "image" refers to a visible depiction or other representation of an item such as the chest area of a patient. In various embodiments presented herein, images provide representations of morphologies and/or compositions of tissue, bone, or organs in a subject. Such images are sometimes referred to herein as medical images. Medical images of varying modality include without limitation representations of tissue, bone, and/or organs derived from computerized tomography (CT), magnetic resonance imaging (MM), x-ray imaging, positron emission tomography (PET) and other nuclear medicine scans, ultrasound imaging, and two-dimensional and/or three-dimensional reconstructions of any of the foregoing. An image may be composed of and/or transformed to three-dimensional image data formed of voxels.

As used herein, a "lung" refers to a single lung organ as present in any vertebrate animal.

As used herein, a "pulmonary artery" is a blood vessel that carries deoxygenated blood into the lung.

As used herein, a "pulmonary vein" is a blood vessel that carries oxygenated blood out of the lung.

As used herein, "vasculature" or "blood vessel" may be used interchangeably to refer to either a pulmonary artery or a pulmonary vein.

As used herein, a lung "airway" refers to an anatomical structure that carries air into and out of the lung. Parts of the airway include the trachea, the bronchi, and the bronchioles. Airways as used herein refer both to the "lumen", or inside space of the airway, which is composed of air, and the tissue wall of airway surrounding the lumen.

As used herein, a "lobe" refers to a lobe within a lung.

As used herein, a "segment" refers to a segment within a lobe.

As used herein, the lung "surface" refers to the exterior surface of a lung.

As used herein, a lung "lesion" refers to any abnormal tissue within the lung, which may be malignant, benign, or of uncertain malignancy. Herein the term lesion may be used interchangeably with the term "mass," which is typically used in the context of larger lung lesions, and "nodule," which is typically used in the context of a smaller lung lesion.

As used herein, the lung "parenchyma" refers to lung tissue which is not an airway, a pulmonary artery, or a pulmonary vein.

As used herein, the term "segmentation" refers to the process of identifying a structure of interest within a medical image, e.g., an anatomical structure such as an organ, lesion, or blood vessel. When segmentation occurs in a three-dimensional medical image, a three-dimensional representation of a structure of interest is created, which may be referred to as a "3D reconstruction".

As used herein, the term "labeling" refers to the process of identifying the nature of a structure that has been segmented and assigning a relevant semantic name to such structure.

As used herein, the term "voxel," or volumetric pixel, refers to a single, discrete point in a regular grid in three-dimensional space. In medical images, voxels are typically rectangular prisms, and each has an intensity value (corresponding to a value on a grey or multi-colored scale).

As used herein, the term "plane" refers to a surface in a Euclidean or other space. The surface has no volume. It need not be "flat" as with a Euclidean plane.

VII. Identification of Anatomical Structures within Medical Images (Excluding Lung Segments)

This section describes various examples of methods to segment and label anatomical structures within medical images of lungs.

Among the relevant structures within medical images of lungs are: lung surfaces, lung parenchyma, pulmonary arteries, pulmonary veins, airways, lung lobes, and lung fissures. The representations of some or all of these structures are inputs to the system and methods described in Section VIII which identify the boundaries between lung segments and which are the subject of the present disclosure.

The airways and pulmonary vasculature of the lung each form a tree-like branching network of tubular structures. One method for segmenting airways and vasculature from three-dimensional medical images is based on the mathematical properties of these tube-like structures. Such method may, in some implementations, merely segment, but not label, tube-like anatomical features. Labeling may be accomplished in a subsequent operation. Methods that analyze images based on these properties include, without limitation, graph-based optimization, Hessian calculations, and flux-based methods. These techniques identify regions of voxels (e.g. a ten by ten by ten cube of voxels within a larger image) where a mathematical operation on that region, such as a Hessian calculation, returns a positive result indicating that the high intensity voxels within that region are in a tubular shape. Examples of such techniques are described by Benmansour 2011, Benmansour 2013, Antiga 2007, Graham 2010, and Helmberger 2014.

Another method to segment airways and pulmonary vasculature is based on a machine learning model, which may also be used to merely segment or segment and label such structures. An appropriate training algorithm, based on any one of several supervised machine learning algorithms, may be used to train a machine learning model using information such as prior segmentations and labelings of airways and vessels. The training algorithm may be used to recognize patterns in the images to accurately identify airways and vessels and/or assign labels to such structures. An example of such technique is described by Ochs 2007.

In some implementations, structures that have been segmented as tubular structures, such as by using graph-based optimization, Hessian calculations, or flux-based methods, may be analyzed and assembled into a tree-like structure that represents an interconnected system of veins, arteries, and/or airways. One approach to such analysis may involve the use of a non-linear integer program to be solved by a non-linear solver. Another approach may utilize a machine learning model. In general, these approaches fit a number of candidate voxels to a model of a tree-like structure. When a non-linear solver is used, such model is represented by non-linear equations; when machine learning is used, the model is the machine learning model which has been trained with examples of tree-like structures. Examples of similar techniques are described by Turetken 2013, Turetken 2016, Payer 2015, and Payer 2016.

Once a tree-like structure has been assembled, a separate technique such as a machine learning model may be used to label the applicable structures comprising such tree-like structure. For example, such technique may receive partially processed image data containing one or more pre-segmented tree-like anatomical structures that could be veins, arteries, and/or airways. The technique then analyzes the tree-like structures and classifies or otherwise labels them as veins, arteries, and/or airways.

Aside from machine learning, another method to label a structures that includes an assembled tree-like structure is to take, as input, a non-linear integer program that represents the segmented artery, vein, and airway structures. That program is analyzed by a non-linear solver to assign labels to each of the segmented structures. An example of such technique is described by Payer 2016.

As an alternative to labeling structures only after they have been segmented, other methods that may be used to segment and label structures during the same process. For example, one technique which is specialized for the segmentation of airways will generate segmented structures that are labeled as airways. Examples of such techniques are described by van Ginneken 2008 and Meng 2018, Pu 2010.

In some embodiments, lung anatomical structures are identified using atlas segmentation, which is a technique that can be used for the segmentation and labeling not only for airways and vessels but also for many other anatomical features such as lung surface. For the remainder of this paragraph, segmentation may refer equally to segmentation only or to segmentation and labelling as part of the same process. In atlas segmentation, an image to be segmented (input) is compared against each image contained in a database of previously segmented images (the atlas). Atlas segmentation will identify the image within the atlas which is most "similar" to the input image. In this instance, "similarity" is based on the degree of transformation required to "register" the input image to the image in the atlas (meaning, align one image to the other). The smaller the degree of transformation required between two images, the more similar those two images are. Multiple similarity metrics are possible, including sum of squared distances, correlation coefficients, and mutual information. Once the most similar atlas image is identified, the nature of the transformation between the atlas image and the input image is determined. Multiple transformation models are possible, including rigid, affine, and deformable transformation models. Once the nature of the transformation is determined, that transformation is applied to the segmentation of the atlas image which results in a segmentation of the input image. An example of such technique is described by Rohlfing 2004.

This paragraph and a few following paragraphs discuss optional techniques for the identification of the lung surface. One method to identify the surface of the lung utilizes atlas segmentation. It compares the input image of the lung to an atlas of previously segmented lung images, determining the most similar atlas lung image, then determining the transformation from the atlas image to the input image, then applying that transformation to the segmentation of the atlas image to generate the segmentation of the input image lung surface.

Another method to identify the surface of the lung is through voxel intensity gradient analysis. This analysis considers voxel intensity gradients within the image, meaning, changes in voxel intensity over a range of contiguous voxels within an image. In CT scans and MM images, lung parenchyma shows up as voxels of low intensity, and the exterior of the lung surface shows up as voxels of higher intensity. A rapidly changing gradient is indicative of a lung surface.

Another method to identify the surface of the lung is to utilize a machine learning model. This machine learning model would be trained with segmentations of the lung surface, along with the images from which those segmentations were generated. It would analyze the voxels within an input image to accurately predict which voxels correspond to the lung surface.

This paragraph and the next describe the identification of lung fissures. One method to identify fissures is through voxel intensity analysis. Fissures can be identified based on gradient analysis, with the analysis identifying voxel intensity changes between parenchyma voxels and fissure voxels, or by identifying voxels that constitute plane-like structures with hessian eigenvalue and eigenvector analysis. An example of a similar technique is described by Lassen 2013.

Another method to identify fissures involves the detection of "planes" (which are three-dimensional surfaces without a volume) through vasculature and/or airway voxel density analysis. Fissures can be represented as planes. One property of fissures is that the density of vasculature and airways is lower around fissures than around parenchyma. One method of finding fissures in lungs is to determine which planes have the lowest density of surrounding voxels which correspond to airways, arteries, and veins. Those planes may be taken to be the representation of the fissures, or may be adjusted in space to align with fissures identified using the gradient-based method described in the preceding paragraph.

This paragraph and the next two discuss the identification of lung parenchyma. One method to identify the lung parenchyma is a subtraction-based method. This method starts by identifying the lung surface and the three-dimensional space occupied within such lung surface. From this three-dimensional space, the three-dimensional space occupied by the vessels, airways and fissures is removed (subtracted). The resulting difference represents a segmentation of the lung parenchyma.

Another method to identify lung parenchyma is via analysis of voxel intensity variation and connectivity, which is the way in which voxels relate to adjacent voxels of similar intensity. This analysis involves identifying voxels that are low in intensity value and which are highly connected to other voxels also low in intensity value. Low intensity voxels associated with airway lumens are then removed.

Another method to identify the lung parenchyma is through Otsu's method of thresholding. Otsu's method determines a single intensity threshold that separates voxels into "foreground" and "background" voxels while minimizing variance between the two groups; in the case of images of lungs, those correspond to low intensity parenchyma voxels within the surface and high intensity voxels exterior to the lung surface. An example of such technique is described by Helen 2011.

The remaining paragraphs within this section discuss the identification of lung lobes. One method to identify lung lobes is to start with (a) the segmented lung parenchyma and/or (b) the identified lung surface, and then subdividing the applicable structure according to identified lung fissures in either or both (a) and (b).

Another method to identify lung lobes employs an algorithm such as a watershed algorithm to pulmonary arteries. The method takes as input a segmentation of the pulmonary arteries. It then identifies each lobar branch of the pulmonary arteries (and the subtree associated with such branch) using the following approach: arterial branches that appear within the segmented pulmonary arteries are matched to common branching variants of lung anatomy contained within predefined abstract representations of arterial anatomy. Alternatively, lobar branches of pulmonary arteries may be identified via a k-means clustering algorithm, where the branches of the tree are partitioned into multiple clusters, and each cluster corresponds to a different lobar branch. Areas identified as artery subtrees are considered "high cost" areas within a "cost image" which is used as an input to a watershed algorithm to determine the planes which are equidistant to the edges of each of the subtrees, or, analogously, which are "lowest cost" by the input cost image. An example of such technique is described by Beucher 1992.

Another method to identify lung lobes is based on the application of a watershed algorithm to pulmonary veins. It takes as input a segmentation of the pulmonary veins. It then identifies each lobar branch of the pulmonary veins (and the subtree associated with such branch) using the following approach: venous branches that appear within the segmented pulmonary veins are matched to common branching variants of lung anatomy contained within predefined abstract representations of venous anatomy. Alternatively, lobar branches of pulmonary veins may be identified via a k-means clustering algorithm, where the branches of the tree are partitioned into multiple clusters, and each cluster corresponds to a different lobar branch. Areas identified as pulmonary veins subtrees are considered "high cost" areas within a "cost image" which is used as an input to a watershed algorithm to determine the planes which are equidistant to the edges of each of the subtrees, or, analogously, which are "lowest cost" by the input cost image.

Another method to identify lung lobes is based on the application of a watershed algorithm to airways. It takes as input a segmentation of the airways. It then identifies each lobar branch of the airways (and the subtree associated with such branch) using the following approach: airway branches that appear within the segmented airways are matched to common branching variants of lung anatomy contained within predefined abstract representations of airway anatomy. Alternatively, lobar branches of airways may be identified via a k-means clustering algorithm, where the branches of the tree are partitioned into multiple clusters, and each cluster corresponds to a different lobar branch. Areas identified as airway subtrees are considered "high cost" areas within a "cost image" which is used as an input to a watershed algorithm to determine the planes which are equidistant to the edges of each of the subtrees, or, analogously, which are "lowest cost" by the input cost image. An example of a technique to determine lobar branches of airways is described by Gu 2012.

Another method to identify lung lobes is based on the application of a watershed algorithm to a combination of at least two of pulmonary arteries, pulmonary veins, and airways. Another method to identify lung lobes is based on any of the methods discussed above in combination with a cost image where areas with fissures are also deemed "high cost".

Another way to identify the lung lobes is with atlas segmentation. In this case, the atlas contains source medical images (CT, MR, etc.) and/or 3D reconstructions of lungs. The 3D reconstructions may contain the lung surface and may also contain arteries, airways, and/or veins. The input to be compared to the atlas may be a standard medical image (CT, MR, etc.) and/or a 3D reconstruction of such image. The atlas image that is most similar to the input image is determined. Then the transformation from the atlas image to the input image is determined. Then that transformation is applied, in reverse, to the lobe representation of the atlas image to arrive at the lobe representation of the input lung image.

Another method to determine lung lobes is to combine any number of the above methods. Examples of similar techniques are described by Lassen 2013 and Giuliani 2018.

VIII. Identification of Segment Boundaries

This section describes the present disclosure, which is a system and method that enables a computer system to identify and label lung segments from a three-dimensional medical image, and to visually depict such lung segments within a 3D reconstruction.

This paragraph and the next discuss identifying segment boundaries by locating planes that represent the boundaries between adjacent lung segments. One method begins by analyzing a representation of a lobe and its pulmonary artery subtree to identify the segmental branches of such subtree, as in the following approach: arterial branches that appear within the segmented lobar subtree of pulmonary arteries are matched to common branching variants of lung anatomy contained within predefined abstract representations of arterial anatomy. Alternatively, segmental branches of pulmonary arteries may be identified via a k-means clustering algorithm, where the branches of the lobar subtree are partitioned into multiple clusters, and each cluster corresponds to a different segmental branch. Then, after identifying those segmental branches, it determines the lobe's segmental artery subtree. Then, it identifies the planes that are equidistant between each of the arterial subtrees that are contained in adjacent lung segments. Each identified plane represents at least a portion of the boundary between such segments.

Another method begins by analyzing a representation of a lobe and its airway subtree to identify the segmental branches of such subtree as in the following approach: airway branches that appear within the segmented lobar subtree of airways are matched to common branching variants of lung anatomy contained within predefined abstract representations of airway anatomy. Alternatively, segmental branches of airways may be identified via a k-means clustering algorithm, where the branches of the lobar subtree are partitioned into multiple clusters, and each cluster corresponds to a different segmental branch. Then, after identifying those segmental branches, it determines the lobe's segmental airway subtree. Then, it identifies the planes that are equidistant between each of the airway subtrees that are contained in adjacent lung segments. Each identified plane represents at least a portion of the boundary between such segments.

This paragraph and a few subsequent paragraphs discuss identifying segment boundaries by identifying planes based on the location of intersegmental veins. This method analyzes a representation of a lobe and a representation of the lobe's pulmonary vein subtree to identify the intrasegmental and intersegmental veins within that lobe as in the following approach: venous branches that appear within the segmented lobar subtree of pulmonary veins are matched to common branching variants of lung anatomy contained within predefined abstract representations of venous anatomy. Each identified intersegmental vein branch is a line or other path which lies on the plane that defines the boundary between two adjacent segments (the "intersegmental plane"). After identifying this line, the system identifies such plane using, e.g., one of the methods described in the following paragraphs.

The first example method to identify the intersegmental plane is via a watershed algorithm, which assumes that the plane is equidistant to the edges of subtrees of intrasegmental veins, and/or subtrees of pulmonary arteries, and/or subtrees of airways. The plane is then adjusted via surface fitting such that the intersegmental vein will lie on the resulting plane. Examples of surface fitting techniques include least sum of squares fitting, linear and non-linear regression, interpolation, RANSAC, B-Spline surface fitting as described in Liew 2015, and Hough transformations as described by Drost 2015.

The second example method to identify intersegmental planes is via atlas segmentation and adjusted via surface fitting such that the intersegmental veins will lie on the resulting plane.

The third example method to identify intersegmental planes is via by machine learning and adjusting via surface fitting such that the intersegmental veins will lie on the resulting plane.

Another method to generate segment boundaries is via machine learning techniques, directly. In this approach, the machine learning model has been trained with training inputs of three dimensional representations of lungs, which might contain any of: lung surfaces, lung parenchyma, veins, arteries, airways, and fissures, and for which the output is lung segments. This model takes in a three-dimensional representation of a lung without segment boundaries and generates an output that includes segment boundaries.

Another method to generate segment boundaries is with atlas segmentation. Here, the input considered is a three-dimensional representation of a lobe and the atlas constitutes a set of three-dimensional representations of lobes with their corresponding segment boundaries identified. The method compares the input lobe three-dimensional representation to the atlas of lobe three-dimensional representations with segment boundaries identified, determining the most similar lobe three-dimensional representation within the atlas. The transformation from the atlas lobe to the input lobe is determined. The segment boundaries within the atlas lobe have that transformation applied to generate the segment boundaries within the input lobe. In some embodiments, the atlas constitutes a set of three-dimensional representations of a lobe and one or more of airways, arteries, and veins with their corresponding segment boundaries identified.

Another method to generate segment boundaries is by analyzing the density of voxels corresponding to vasculature and airways. Any combination of following lobar subtrees may be considered: lobar subtree of airways, lobar subtree of arteries, lobar subtree of veins. This analysis identifies the planes on the interior of the lung lobe by identifying the airways and/or pulmonary arteries and in particular those areas that have the lowest level of voxel density; a low level of voxel intensity indicates a "channel" through which the plane will run. If considering intersegmental veins, an opposite approach is undertaken; a high level of voxel intensity is indicative of an intersegmental vein, which in turn is indicative of a segment boundary.

If desired, any number of the above-described techniques, such as voxel density analysis, atlas segmentation, machine learning, watershed between subtrees, intersegmental vein location, and surface fitting, may be performed in combination.

IX. Flowcharts of Example Methods of Identifying Lung Features

Figure 5A:
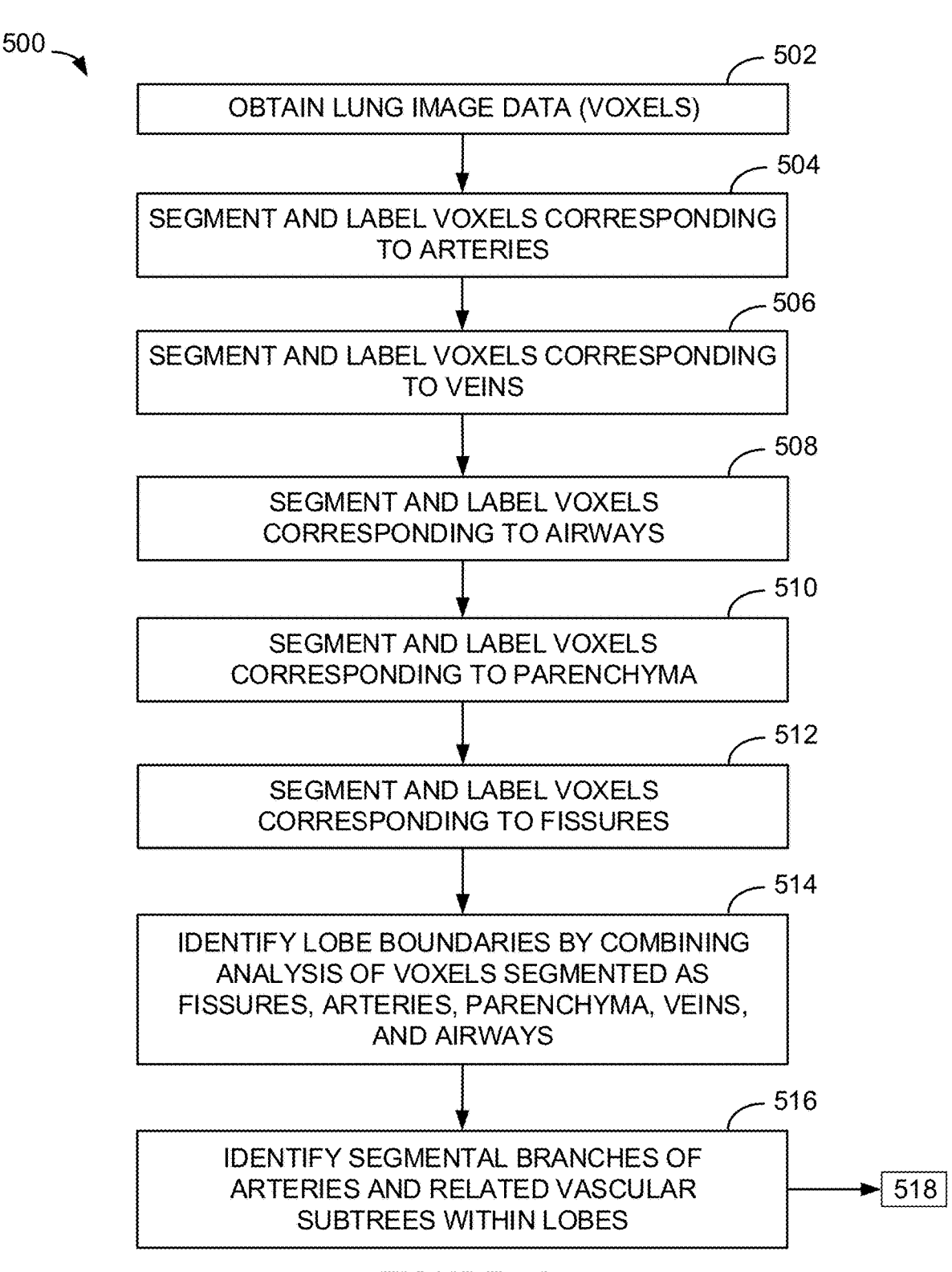

FIGS. 5A and 5B present a flow chart of one embodiment of a method 500 for determining segment boundaries of a lung. As shown, method 500 initially obtains or receives image data for a lung (operation 502). As indicated, this image data may take the form of voxels or other representation of points in a three-dimensional space. As indicated herein, such data may be obtained from various sources such as x-ray images (e.g., CT scans), nuclear magnetic resonance images, and other medical imaging data such as those obtained by positron emission tomography. In various embodiments, the data includes image information for at least an entire segment of a lung.

As illustrated in an operation 504, the method segments and labels the image data provided in operation 502 to identify those voxels or other points that correspond to the location of pulmonary arteries within a lobe or lung. Also, as illustrated in an operation 506, the method segments and labels the voxel data obtained in operation 502 to identify those voxels that correspond to locations of pulmonary veins. Further, in an operation 508, the method segments and labels the image data obtained in operation 502 to identify voxels corresponding to locations of pulmonary airways or airway tissue within a lobe or lung. Also, in an operation 510, the method segments and labels image data obtained in operation 502 to identify voxels within the three-dimensional space of the lobe or lung where parenchyma is located. Further, in an operation 512, the method segments and labels the image data obtained in operation 502 and identifies those voxels that correspond to locations of fissures in the lung.

To this point, method 500 has analyzed three-dimensional image data of a lobe or lung to identify various anatomical features. In the depicted embodiment, these features are pulmonary arteries, pulmonary veins, pulmonary airways, parenchyma, and lobe or lung fissures. This is not an exhaustive list. The method may analyze the image data to identify one or more other anatomical features such as lymph nodes or lesions. Further, in some implementations, the method does not identify each of the pulmonary arteries, pulmonary veins, pulmonary airways, parenchyma, and lobe or lung fissures. In other words, while the depicted embodiment shows that operations 504 through 512 are performed in the depicted method, this is not required. In some embodiments, any one or more of these anatomical features are segmented and labeled for use in subsequent operations. In certain embodiments, the fissures, the airways, the parenchyma, and the arteries are segmented and labeled, while the veins are not segmented and labeled. In some embodiments, the veins, parenchyma, and airways are segmented and labeled, while the arteries and fissures are not segmented and labeled. In some embodiments, the parenchyma, the fissures, the veins, and the arteries are segmented and labeled, while the airways are not segmented and labeled. In some embodiments, the parenchyma, the fissures, the veins, and the airways are segmented and labeled, while the arteries are not segmented and labeled. In some embodiments, the parenchyma, the airways, the veins, and the arteries are segmented and labeled, while the fissures are not segmented and labeled. In some embodiments, the parenchyma, the arteries, and the airways are segmented and labeled, while the veins and fissures are not segmented and labeled.

In the depicted embodiment, the method next uses one or more of the segmented and labeled anatomical features including the lung fissures, the parenchyma, the pulmonary airways, the pulmonary veins, and/or the pulmonary arteries in order to locate lobe boundaries in the three-dimensional space representing the lung (operation 514). In certain embodiments, the method employs only a subset of the listed operations to identify lobe boundaries. For example, the method may employ only the lung fissures, parenchyma, and arteries. In certain embodiments, and depending on the lung under consideration, operation 514 may be repeated to locate multiple lobe boundaries in the lung under consideration.

Next, in the depicted embodiment, at an operation 516, the method identifies segmental branches and related subtrees of the pulmonary arteries identified in operation 504. Additionally, in the depicted embodiment, at an operation 518, the method identifies segmental branches and related subtrees of the pulmonary arteries identified in operation 508. When the method identifies the branch that leads into a given segment, it can trace the artery network downstream to identify the full tree of an arterial or airway network within a segment. Further, in an operation 520 of the depicted process, the method identifies one or more intersegmental branches of veins within lobes. The intersegmental branches are identified from the veins identified in operation 506.

Next, in an operation 522 of the depicted embodiment, the method uses any one or more of the segmental features identified in operations 516, 518, and 520, optionally along with the parenchyma, to determine at least a portion of the boundaries for a given segment. Note that these operations 516, 518, 520, and 522 are performed within a given lobe, which contains multiple segments. Operation 522 identifies a boundary between two adjacent segments in a lobe. It does not necessarily identify the full boundary of a segment. In various embodiments and depending on how many segments reside in a given lobe, the method repeats operation 522 to generate intersegmental boundaries between multiple segments (sometimes all segments) in a lobe under consideration.

Next, in an operation 524 of the depicted embodiment, the method uses some or all of the intersegmental boundaries identified in operation 522 along with some or all of the lobe boundaries identified in operation 514 to identify the all or substantially all of the lung segment boundaries for at least one segment within a lobe.

Finally, in an operation 526, the method generates a representation of the lung or lobe showing some or all the segment boundaries identified in operation 524, optionally along with lobe boundaries identified in operation 514.

Note that the segment boundaries include interior portions within a lobe interior and surface portions on the lobe surface. In some cases, the method uses the same technique to identify both the interior and surface portions of the segment boundaries. The relevant technique is employed in operation 522 of the depicted embodiment.

Figure 6A:
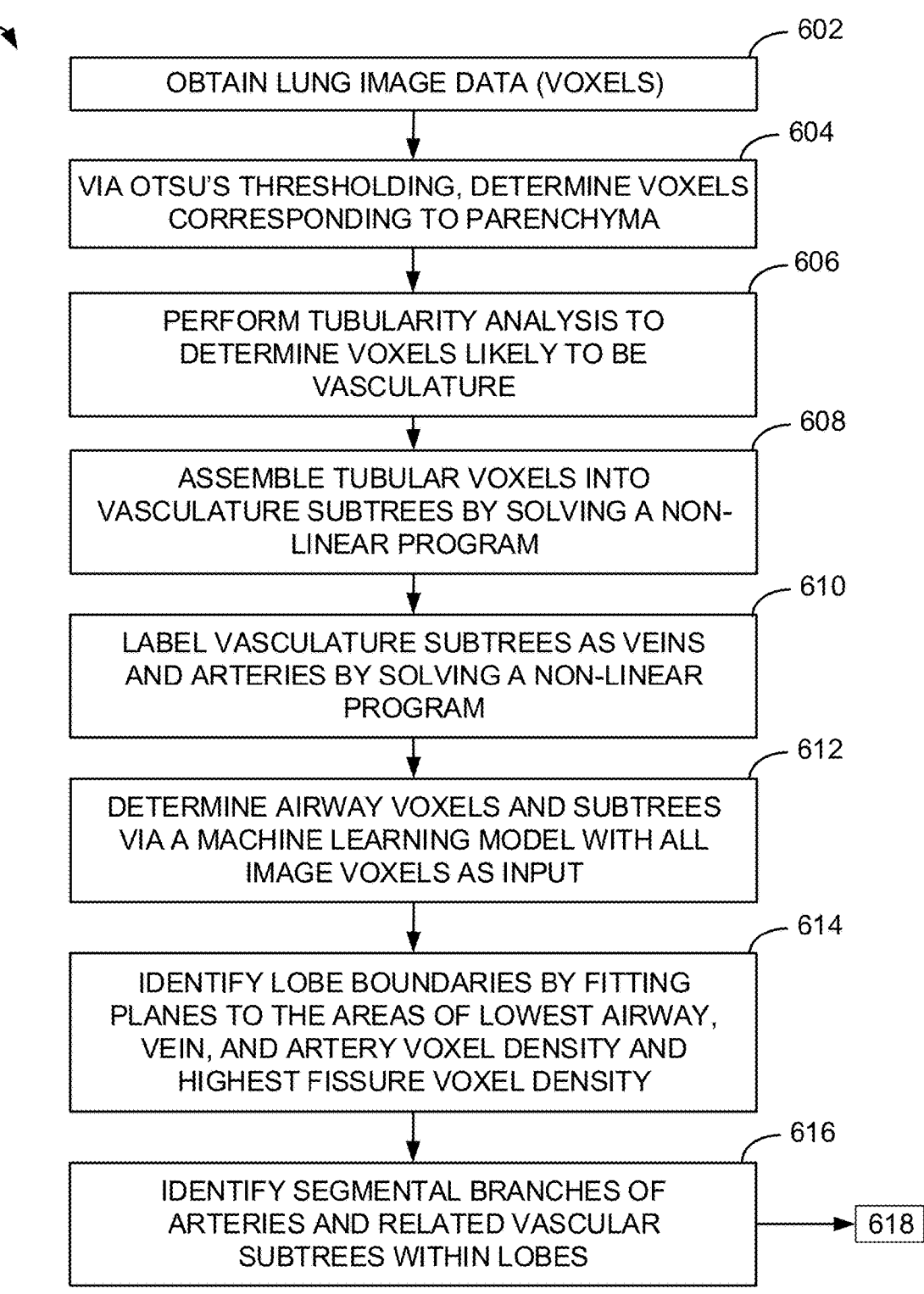

FIGS. 6A and 6B present a flow chart of another embodiment of a method 500 for identifying and optionally representing boundaries of one or more lung segments. Some of the operations are similar to those shown in FIGS. 5A and 5B. For example, operation 510 (segmenting and labeling parenchyma) may be implemented using Otsu's thresholding. As another example, the operations 504 and 506 that involve segmenting and labeling voxels corresponding to arteries and veins may be implemented by performing tubularity analysis to identify voxels likely to be vasculature, followed by assembling such voxels (tubular collections of voxels) into subtrees using a non-linear program, and, ultimately, labelling the subtrees as veins and arteries using a non-linear program. As a further example, operation 508, which involves segmenting and labelling voxels corresponding to airways may be implemented using a machine learning model with all image voxels as inputs.

In method 600, lobe boundaries are identified by fitting planes to (1) areas of low airway, vein, and/or artery voxel density, and (2) high fissure voxel density. The method also identifies branches of arteries and arterial subtrees within particular segments of a lobe. The method also identifies branches of airways and airway subtrees within particular segments of a lobe. Still further, the method also identifies intersegmental veins within particular segments of a lobe. In the depicted embodiment, the method uses cost images and a watershed algorithm to identify planes between segmental airways and arterial sub-trees. The voxels of airways and arteries are rendered as high cost voxels.

In the depicted embodiment, the method then fits the planes to intersegmental veins between adjacent segments. This allows the method to identify boundaries between adjacent segments within the same lobe. The method then uses these boundaries and the lobe boundaries to define full lung segment boundaries. Ultimately, the method may generate a representation of the lung or lobe with substantially complete segment boundaries.

As shown, method 600 may include one or more of, as examples, obtaining lung image data (operation 602); determining voxels corresponding to parenchyma, optionally via Otsu's thresholding (operation 604); performing tubularity analysis to determine voxels likely to be vasculature (operation 606); assembling tubular voxels into vasculature subtrees by solving a non-linear program (operation 608); labeling vasculature subtrees as veins and arteries by solving a non-linear program (610); determining airway voxels and subtrees via a machine learning model with all image voxels as input (operation 612); identifying lobe boundaries by fitting planes to the areas of lowest airway, vein, and/or artery voxel density and/or the highest fissure voxel density (operation 614); identifying segmental branches of arteries and related vascular subtrees within lobes (operation 616); identifying segmental branches of airways and related subtrees of airways within lobes (operation 618); identifying intersegmental veins within lobes (operation 620); initialize a cost image for each segmental boundary between two adjacent segments within a lobe (operation 622); updating each cost image, rendering voxels of arterial and airway subtrees as high cost (operation 624); running a watershed algorithm to identify planes equidistance to segmental airway and artery subtrees (operation 626); fitting planes to intersegmental veins between adjacent segments to identify boundaries between segments within the same lobe (operation 628); using boundaries between segments within the same lobe and lobe boundaries to define full lung segment boundaries (operation 630); and generating a representation of the lung with identification of the lung lobes and substantially complete segment boundaries (operation 632).

Note that method 600 need not be implemented as an example of the method 500. The operations presented in method 600 need not correspond to particular operations in method 500. The above discussion linking some operations of method 600 to operations of method 500 is provided as an example.

The methods of FIGS. 5A, 5B, 6A, and 6B may be implemented using various forms of image processing or image analysis logic such any combination of the computational techniques described above. The image analysis logic may be hosted on a single computational machine or distributed across multiple machines, optionally including some components that execute locally and others that execute remoted, e.g., via cloud-based resources.

X. Additional Details

The various processes, algorithms, software, etc. disclosed herein may be implemented with, executed on, or otherwise performed by a computing system having various hardware and software elements.

The hardware components may include processors, controllers, storage devices, and the like and may be implemented locally or remotely (including on the cloud).

Software components may be expressed (or represented) as data and/or instructions embodied in various computer-readable media, in terms of their behavioral, logical, and/or other characteristics. Computer-readable media in which such formatted data and/or instructions may be embodied include, but are not limited to, non-volatile storage media in various forms (e.g., optical, magnetic or semiconductor storage media). The computer-readable media corresponding to such systems are also intended to fall within the scope of the present disclosure.

Reference herein to "one embodiment" or "an embodiment" means that a particular feature, structure, or characteristic described in connection with the embodiment can be included in one some or all of the embodiments of the present disclosure. The usages or appearances of the phrase "in one embodiment" or "in another embodiment" in the specification are not referring to the same embodiment, nor are separate or alternative embodiments necessarily mutually exclusive of one or more other embodiments. The same applies to the term "implementation." The present disclosure is neither limited to any single aspect nor embodiment thereof, nor to any combinations and/or permutations of such aspects and/or embodiments. Moreover, each of the aspects of the present disclosure, and/or embodiments thereof, may be employed alone or in combination with one or more of the other aspects of the present disclosure and/or embodiments thereof. For the sake of brevity, certain permutations and combinations are not discussed and/or illustrated separately herein.

Further, an embodiment or implementation described herein as exemplary is not to be construed as preferred or advantageous, for example, over other embodiments or implementations; rather, it is intended to convey or indicate that the embodiment or the embodiments are example embodiment(s).

In the examples, the term "determine" and other forms thereof (i.e., determining, determined and the like or calculating, calculated and the like) means, among other things, calculate, assesses, determine and/or estimate and other forms thereof.

In addition, the terms "first," "second," and the like, herein do not denote any order, quantity, or importance, but rather are used to distinguish one element from another. Moreover, the terms "a" and "an" herein do not denote a limitation of quantity, but rather denote the presence of at least one of the referenced item. Further, the terms "data" and "metadata" may mean, among other things information, whether in analog or a digital form (which may be a single bit (or the like) or multiple bits (or the like)).

As used in the examples, the terms "comprises," "comprising," "includes," "including," "have," and "having" or any other variation thereof, are intended to cover a non-exclusive inclusion, such that a process, method, article, or apparatus that comprises a list of elements does not include only those elements but may include other elements not expressly listed or inherent to such process, method, article, or apparatus.

The example elements that do not recite "means" or "step" are not in "means plus function" or "step plus function" form. (See, 35 USC § 112(f)). Applicant's intend that only example elements reciting "means" or "step" be interpreted under or in accordance with 35 U.S.C. § 112(f).

In the foregoing description, numerous specific details are set forth to provide a thorough understanding of the presented implementations. The disclosed implementations may be practiced without some or all of these specific details. In other instances, well known process operations have not been described in detail to not unnecessarily obscure the disclosed implementations. While the disclosed implementations are described in conjunction with the specific implementations, it will be understood that it is not intended to limit the disclosed implementations.

Although the foregoing embodiments have been described in some detail for purposes of clarity of understanding, it will be apparent that certain changes and modifications may be practiced within the scope of the appended examples. It should be noted that there are many alternative ways of implementing the processes, systems, and apparatus of the present embodiments. Accordingly, the present embodiments are to be considered as illustrative and not restrictive, and the embodiments are not to be limited to the details given herein.

XI. Additional Disclosures

The following publications are hereby incorporated herein by reference in their entireties. To the extent that these references are present in the body of this disclosure, they are incorporated for at least the purpose and/or context presented in corresponding disclosure.

Benmansour, Fethallah, and Laurent D. Cohen. "Tubular structure segmentation based on minimal path method and anisotropic enhancement." International Journal of Computer Vision 92.2 (2011): 192-210.

Benmansour, Fethallah, Engin Türetken, and Pascal Fua. Tubular geodesics using oriented flux: An ITK implementation. No. ARTICLE. 2013.

Gu, Suicheng, et al. "Automated lobe-based airway labeling." Journal of Biomedical Imaging 2012 (2012): 1.

Graham, Michael W., et al. "Robust 3-D airway tree segmentation for image-guided peripheral bronchoscopy." IEEE transactions on medical imaging 29.4 (2010): 982-997.

Helmberger, Michael, et al. "Quantification of tortuosity and fractal dimension of the lung vessels in pulmonary hypertension patients." PloS one 9.1 (2014): e87515.

Aurenhammer, Franz. "Voronoi diagrams—a survey of a fundamental geometric data structure." ACM Computing Surveys (CSUR) 23.3 (1991): 345-405.

Cornea, Nicu D., et al. "Computing hierarchical curve-skeletons of 3D objects." The Visual Computer 21.11 (2005): 945-955.

van Ginneken, Bram, Wouter Baggerman, and Eva M. van Rikxoort. "Robust segmentation and anatomical labeling of the airway tree from thoracic CT scans." International Conference on Medical Image Computing and Computer-Assisted Intervention. Springer, Berlin, Heidelberg, 2008.

Meng, Qier, et al. "Airway segmentation from 3D chest CT volumes based on volume of interest using gradient vector flow." Medical Imaging Technology 36.3 (2018): 133-146.

Antiga, Luca. "Generalizing vesselness with respect to dimensionality and shape." The Insight Journal 3 (2007): 1-14.

Lassen, Bianca, et al. "Automatic segmentation of the pulmonary lobes from chest CT scans based on fissures, vessels, and bronchi." IEEE transactions on medical imaging 32.2 (2012): 210-222.

Law, Max W K, and Albert C S Chung. "Three dimensional curvilinear structure detection using optimally oriented flux." European conference on computer vision. Springer, Berlin, Heidelberg, 2008.

Giuliani, Nicola, et al. "Pulmonary Lobe Segmentation in CT Images using Alpha-Expansion." VISIGRAPP (4: VISAPP). 2018.

Payer, Christian, et al. "Automatic artery-vein separation from thoracic CT images using integer programming." International Conference on Medical Image Computing and Computer-Assisted Intervention. Springer, Cham, 2015.

Payer, Christian, et al. "Automated integer programming based separation of arteries and veins from thoracic CT images." Medical image analysis 34 (2016): 109-122.

Pu, Jiantao, et al. "A differential geometric approach to automated segmentation of human airway tree." IEEE transactions on medical imaging 30.2 (2010): 266-278.

Shekhovtsov, Alexander, Paul Swoboda, and Bogdan Savchynskyy. "Maximum persistency via iterative relaxed inference with graphical models." Proceedings of the IEEE Conference on Computer Vision and Pattern Recognition. 2015.

Turetken, Engin, et al. "Reconstructing loopy curvilinear structures using integer programming." Proceedings of the IEEE Conference on Computer Vision and Pattern Recognition. 2013.

Türetken, Engin, et al. "Reconstructing curvilinear networks using path classifiers and integer programming." IEEE transactions on pattern analysis and machine intelligence 38.12 (2016): 2515-2530.

van Dongen, Evelien, and Bram van Ginneken. "Automatic segmentation of pulmonary vasculature in thoracic CT scans with local thresholding and airway wall removal." 2010 IEEE International Symposium on Biomedical Imaging: From Nano to Macro. IEEE, 2010.

Ochs, Robert A., et al. "Automated classification of lung bronchovascular anatomy in CT using AdaBoost." Medical image analysis 11.3 (2007): 315-324.

Rohlfing, Torsten, et al. "Evaluation of atlas selection strategies for atlas-based image segmentation with application to confocal microscopy images of bee brains." NeuroImage 21.4 (2004): 1428-1442.

Beucher, Serge. "The watershed transformation applied to image segmentation." SCANNING MICROSCOPY-SUPPLEMENT-(1992): 299-299.

Helen, R., et al. "Segmentation of pulmonary parenchyma in CT lung images based on 2D Otsu optimized by PSO." 2011 International Conference on Emerging Trends in Electrical and Computer Technology. IEEE, 2011.

Shirk, Joseph D., et al. "Effect of 3-Dimensional Virtual Reality Models for Surgical Planning of Robotic-Assisted Partial Nephrectomy on Surgical Outcomes: A Randomized Clinical Trial." JAMA network open 2.9 (2019): e1911598-e1911598.

Drost, Bertram, and Slobodan Ilic. "Local hough transform for 3d primitive detection." 2015 International Conference on 3D Vision. IEEE, 2015.

XII. Conclusion

Although the foregoing embodiments have been described in some detail for purposes of clarity of understanding, it will be apparent that certain changes and modifications may be practiced within the scope of the appended claims. It should be noted that there are many alternative ways of implementing the processes, systems, and apparatus of the present embodiments. Accordingly, the present embodiments are to be considered as illustrative and not restrictive, and the embodiments are not to be limited to the details given herein.

What is claimed is:

1. A method of determining segment boundaries of lung segments, the method comprising:

receiving image data forming a three-dimensional representation of at least a part of a lung, wherein the lung is divided into multiple lung lobes, wherein each lobe is divided into multiple lung segments;

computationally identifying, using the image data, at least one anatomical feature within the lung, wherein the at least one anatomical feature comprises one or more of the following: a network of arteries, a network of veins, a network of airways, some or all of lung parenchyma, and one or more fissures of the lung;

computationally identifying, using the at least one anatomical feature, all segment boundaries of at least one lung segment within the lung, wherein the segment boundaries comprise surfaces between the at least one lung segment and adjacent lung segments; and generating a representation of all or part of the lung showing the segment boundaries of the at least one lung segment within the lung.

2. The method of claim 1, wherein the image data comprises a one or both of a CT scan and an MRI.

3. The method of claim 1, wherein the at least one anatomical feature comprises some or all of the lung parenchyma and the network of arteries.

4. The method of claim 1, wherein the at least one anatomical feature comprises some or all of the lung parenchyma and the network of veins.

5. The method of claim 1, wherein the at least one anatomical feature comprises some or all of the lung parenchyma and the network of airways.

6. The method of claim 1, wherein the at least one anatomical feature comprises the one or more fissures of the lung.

7. The method of claim 1, wherein computationally identifying all segment boundaries of the at least one lung segment comprises:

computationally identifying, using the at least one anatomical feature, one or more of the following: segmental branches of arteries and related subtrees, segmental branches of veins, segmental branches of airways and related subtrees, and the fissures of the lung;

generating segment boundaries between adjacent lung segments in the lung through analysis of segmental branches of arteries and related subtrees, segmental branches of veins, segmental branches of airways and related subtrees, and/or fissures of the lung; and combining the segment boundaries between adjacent lung segments to define all of the segment boundaries of the at least one lung segment within the lung.

8. The method of claim 1, further comprising:

computationally identifying, using the at least one anatomical feature, lobe boundaries for a plurality of lobes in the lung.

9. The method of claim 1, further comprising:

computationally identifying, using the image data, a lesion within the lung; and computationally determining, from the image data, that the lesion is located in a given lung segment of the at least one lung segment or in a region spanning two or more lung segments.

10. The method of claim 9, further comprising:

computationally measuring, from the image data, a minimum distance between the lesion and a segment boundary of any of the lung segments.

11. A method of identifying segment boundaries of lung segments, the method comprising:

receiving image data forming a volumetric representation of at least a part of a lung, wherein the lung is divided into multiple lobes, wherein each lobe is divided into multiple lung segments;

computationally identifying, using the image data, a network of arteries;

computationally identifying, using the image data, a network of bronchi;

computationally identifying, using the image data, a network of veins; and computationally identifying, based on the identified network of arteries, network of bronchi, and network of veins, segment boundaries of a plurality of lung segments within at least one lobe of the lung, wherein the segment boundaries comprise surfaces between adjacent lung segments.

12. The method of claim 11, wherein the image data comprises one or both of a CT scan and an MRI.

13. The method of claim 11, wherein computationally identifying the network of arteries comprises:

computationally identifying a tube-like structure in the image data, wherein the tube-like structure is identified by identifying a set of gradient changes within the image data; and computationally determining, using the image data and based on how the tube-like structure branches within the lung, that the tube-like structure is part of the network of arteries.

14. The method of claim 11, wherein computationally identifying the network of bronchi comprises:

computationally identifying a tube-like structure in the image data, wherein the additional tube-like structure is identified by identifying a set of gradient changes within the image data; and computationally determining, using the image data and based on how the additional tube-like structure branches within the lung, that the tube-like structure is part of the network of bronchi.

15. The method of claim 11, wherein computationally identifying the network of veins comprises:

computationally identifying a tube-like structure in the image data, wherein the tube-like structure is identified by identifying a set of gradient changes within the image data; and computationally determining, using the image data and based on how the tube-like structure branches within the lung, that the tube-like structure is part of the network of veins.

16. The method of claim 11, wherein computationally identifying the segment boundaries of the plurality of lung segments comprises:

computationally identifying a volume within the image data that receives blood from a section of the network of arteries.

17. The method of claim 11, wherein computationally identifying the segment boundaries of the plurality of lung segments comprises:

computationally identifying a volume within the image data that receives air from a section of the network of bronchi.

18. The method of claim 11, further comprising:

computationally identifying, using the image data, one or more intersegmental veins; and computationally refining, based on the one or more intersegmental veins, the segment boundaries of the plurality of lung segments of the at least one lobe.

19. A method of determining segment boundaries of lung segments, the method comprising:

receiving image data forming a three-dimensional representation of at least a part of a lung, wherein the lung is divided into multiple lobes, wherein each lobe is divided into multiple lung segments;

computationally identifying, using the image data, one or more intersegmental veins within the lung;

computationally identifying segment boundaries of at least one lung segment within the lung based at least in part on the identified one or more intersegmental veins, wherein the segment boundaries comprise surfaces between the at least one lung segment and adjacent lung segments; and generating a representation of all or part of the lung showing the segment boundaries of the at least one lung segment within the lung.

20. A method of determining segment boundaries of lung segments, the method comprising:

receiving image data forming a three-dimensional representation of at least a part of a lung, wherein the lung is divided into multiple lobes, wherein each lobe is divided into multiple lung segments;

computationally identifying, using the image data, one or more fissures of the lung;

computationally identifying segment boundaries of at least one lung segment within the lung based at least in part on the identified one or more fissures, wherein the segment boundaries comprise surfaces between the at least one lung segment and adjacent lung segments; and generating a representation of all or part of the lung showing the segment boundaries of the at least one lung segment within the lung.

* * * * *